United States Patent
Bakos et al.

(10) Patent No.: US 10,631,860 B2
(45) Date of Patent: Apr. 28, 2020

(54) SURGICAL INSTRUMENT WITH ELECTRICAL CONTACT UNDER MEMBRANE

(71) Applicant: ETHICON LLC, Guaynabo, PR (US)

(72) Inventors: Gregory J. Bakos, Mason, OH (US); Frederick E. Shelton, IV, Hillsboro, OH (US); Gregory G. Scott, Cincinnati, OH (US); Stephen D. Geresy, West Chester, OH (US); Yvan D. Nguetio Tchoumkeu, Blue Ash, OH (US); Amy M. Krumm, Bellbrook, OH (US); Grace E. Waters, Cincinnati, OH (US); Prudence A. Vulhop, Fort Wright, KY (US); Nichole Y. Kwee, Cincinnati, OH (US); John E. Brady, Liberty Township, OH (US); Scott A. Jenkins, Mason, OH (US); Laura A. Schoettmer, Cincinnati, OH (US); Andrew Kolpitcke, Centerville, OH (US); Joshua P. Morgan, Benton, KY (US); Sarah A. Worthington, Maineville, OH (US); Taylor W. Aronhalt, Loveland, OH (US); Alexander R. Cuti, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 124 days.

(21) Appl. No.: 15/934,166

(22) Filed: Mar. 23, 2018

(65) Prior Publication Data

US 2019/0290270 A1 Sep. 26, 2019

(51) Int. Cl.
*A61B 17/072* (2006.01)
*A61B 17/00* (2006.01)
(Continued)

(52) U.S. Cl.
CPC ...... *A61B 17/07207* (2013.01); *A61B 17/072* (2013.01); *A61B 17/068* (2013.01);
(Continued)

(58) Field of Classification Search
CPC ............... A61B 17/068; A61B 17/072; A61B 17/07292; A61B 17/07207; A61B 17/115;
(Continued)

(56) References Cited

U.S. PATENT DOCUMENTS

| | | | | |
|---|---|---|---|---|
| 5,529,235 A | * | 6/1996 | Boiarski | A61B 90/98 227/175.1 |
| 5,624,452 A | * | 4/1997 | Yates | A61B 17/072 606/139 |

(Continued)

FOREIGN PATENT DOCUMENTS

| | | |
|---|---|---|
| EP | 2 165 664 A2 | 3/2010 |
| EP | 2 839 797 A2 | 2/2015 |

(Continued)

OTHER PUBLICATIONS

Hollister, S., "Waterproofing explained: How Apple, Samsung and Sony keep the liquid out," cnet.com, Sep. 21, 2016, downloaded from https://www.cnet.com/news/how-does-waterproofing-work-apple-iphone-7-samsung-galaxy-s7-sony-xperia/, copyrighted by CBS Interactive Inc., 8 pgs.

(Continued)

*Primary Examiner* — Scott A Smith
(74) *Attorney, Agent, or Firm* — Frost Brown Todd LLC

(57) ABSTRACT

A surgical instrument includes a body, a shaft assembly, an end effector, and an electrical contact assembly. The includes a power source, while the shaft assembly extends distally from the body. The end effector includes a channel assembly and a cartridge assembly configured to selectively couple with the channel assembly. The cartridge assembly (Continued)

includes an electrically activated component. The electrical contact assembly is capable of electrically coupling the power source with the electrically activated component of the cartridge assembly. The electrical contact assembly includes a first electrical contact, a second electrical contact, and an insulating membrane. The first electrical contact is associated with the channel assembly while the second electrical contact is associated with the cartridge assembly. The insulating membrane is associated with either the first electrical contact or the second electrical contact. The insulating membrane is configured to transition between a closed position and an opened position. Either the first electrical contact or the second electrical contact is configured to transition the insulation membrane to the opened position when the cartridge assembly is coupled to the channel assembly.

20 Claims, 27 Drawing Sheets

(51) Int. Cl.
    *H01R 4/2404*     (2018.01)
    *H01R 3/08*     (2006.01)
    *A61B 17/068*     (2006.01)

(52) U.S. Cl.
    CPC ............. *A61B 2017/00017* (2013.01); *A61B 2017/0046* (2013.01); *A61B 2017/00398* (2013.01); *A61B 2017/00469* (2013.01); *A61B 2017/00477* (2013.01); *A61B 2017/00734* (2013.01); *A61B 2017/07214* (2013.01); *A61B 2017/07257* (2013.01); *A61B 2017/07271* (2013.01); *A61B 2017/07278* (2013.01); *A61B 2017/07285* (2013.01); *H01R 3/08* (2013.01); *H01R 4/2404* (2013.01); *H01R 2201/12* (2013.01)

(58) Field of Classification Search
    CPC .......... A61B 2017/07214; A61B 2017/07271; A61B 2017/07285; A61B 2017/00017; A61B 2017/00022; A61B 2017/00734; A61B 2017/00398; A61B 2017/00199
    USPC .............. 227/19, 175.2, 176.1, 180.1, 175.1; 606/1, 49, 139, 219
    See application file for complete search history.

(56) References Cited

U.S. PATENT DOCUMENTS

| | | | |
|---|---|---|---|
| 5,792,135 A | 8/1998 | Madhani et al. | |
| 5,817,084 A | 10/1998 | Jensen | |
| 5,817,093 A | 10/1998 | Williamson, IV et al. | |
| 5,878,193 A | 3/1999 | Wang et al. | |
| 6,231,565 B1 | 5/2001 | Tovey et al. | |
| 6,364,888 B1 | 4/2002 | Niemeyer et al. | |
| 6,602,252 B2* | 8/2003 | Mollenauer | A61B 17/07207 227/175.1 |
| 6,783,524 B2 | 8/2004 | Anderson et al. | |
| 7,147,138 B2* | 12/2006 | Shelton, IV | A61B 17/07207 227/176.1 |
| 7,404,508 B2 | 7/2008 | Smith et al. | |
| 7,506,790 B2* | 3/2009 | Shelton, IV | A61B 17/07207 227/175.1 |
| 7,524,320 B2 | 4/2009 | Tierney et al. | |
| 7,559,452 B2* | 7/2009 | Wales | A61B 17/068 227/175.1 |
| 7,691,098 B2 | 4/2010 | Wallace et al. | |
| 7,721,930 B2 | 5/2010 | McKenna et al. | |
| 7,784,663 B2* | 8/2010 | Shelton, IV | A61B 17/072 227/175.1 |
| 7,806,891 B2 | 10/2010 | Nowlin et al. | |
| 8,408,439 B2 | 4/2013 | Huang et al. | |
| 8,414,577 B2* | 4/2013 | Boudreaux | A61B 17/07207 606/34 |
| 8,453,914 B2 | 6/2013 | Laurent et al. | |
| 8,475,474 B2* | 7/2013 | Bombard | A61B 17/115 227/178.1 |
| 8,479,969 B2 | 7/2013 | Shelton, IV | |
| 8,573,461 B2 | 11/2013 | Shelton, IV et al. | |
| 8,573,465 B2 | 11/2013 | Shelton, IV | |
| 8,602,288 B2 | 12/2013 | Shelton, IV et al. | |
| 8,608,045 B2 | 12/2013 | Smith et al. | |
| 8,616,431 B2 | 12/2013 | Timm et al. | |
| 8,783,541 B2 | 7/2014 | Shelton, IV et al. | |
| 8,800,838 B2 | 8/2014 | Shelton, IV | |
| 8,820,605 B2 | 9/2014 | Shelton, IV | |
| 8,844,789 B2 | 9/2014 | Shelton, IV et al. | |
| 8,905,977 B2* | 12/2014 | Shelton | A61B 17/07207 604/131 |
| 8,955,732 B2* | 2/2015 | Zemlok | A61B 17/072 227/176.1 |
| 8,991,678 B2 | 3/2015 | Wellman et al. | |
| 8,998,060 B2 | 4/2015 | Bruewer et al. | |
| 9,072,535 B2 | 7/2015 | Shelton, IV et al. | |
| 9,186,142 B2 | 11/2015 | Fanelli et al. | |
| 9,301,759 B2 | 4/2016 | Spivey et al. | |
| 9,332,974 B2* | 5/2016 | Henderson | A61B 17/00491 |
| 9,345,481 B2 | 5/2016 | Hall et al. | |
| 9,724,094 B2 | 8/2017 | Baber et al. | |
| 9,795,379 B2 | 10/2017 | Leimbach et al. | |
| 9,839,425 B2 | 12/2017 | Zergiebel et al. | |
| 9,913,642 B2 | 3/2018 | Leimbach et al. | |
| 2014/0263541 A1 | 9/2014 | Leimbach et al. | |
| 2014/0263552 A1 | 9/2014 | Hall et al. | |
| 2016/0066911 A1 | 3/2016 | Baber et al. | |
| 2016/0310134 A1 | 10/2016 | Contini et al. | |

FOREIGN PATENT DOCUMENTS

| | | |
|---|---|---|
| EP | 2 923 661 A2 | 9/2015 |
| EP | 3 251 610 A1 | 12/2017 |
| EP | 3 338 693 A2 | 6/2018 |
| WO | WO 2015/153642 A1 | 10/2015 |

OTHER PUBLICATIONS

U.S. Appl. No. 15/635,663, filed Jun. 28, 2017.
U.S. Appl. No. 15/635,631, filed Jun. 28, 2017.
U.S. Appl. No. 15/635,837, filed Jun. 28, 2017.
U.S. Appl. No. 15/636,096, filed Jun. 28, 2017.
U.S. Appl. No. 15/934,139, filed Mar. 23, 2018.
U.S. Appl. No. 15/934,148, filed Mar. 23, 2018.
U.S. Appl. No. 15/934,160, filed Mar. 23, 2018.
U.S. Appl. No. 15/934,173, filed Mar. 23, 2018.
U.S. Appl. No. 15/934,180, filed Mar. 23, 2018.
U.S. Appl. No. 15/934,190, filed Mar. 23, 2018.
European Search Report, Partial, and Provisional Written Opinion dated Jul. 26, 2019 for Application No. EP 19164690.0, 12 pgs.
European Search Report and Written Opinion dated Nov. 20, 2019 for Application No. EP 19164690.0, 11 pgs.
International Search Report and Written Opinion dated Oct. 9, 2019 for Application No. PCT/IB2019/052281, 18 pgs.

* cited by examiner

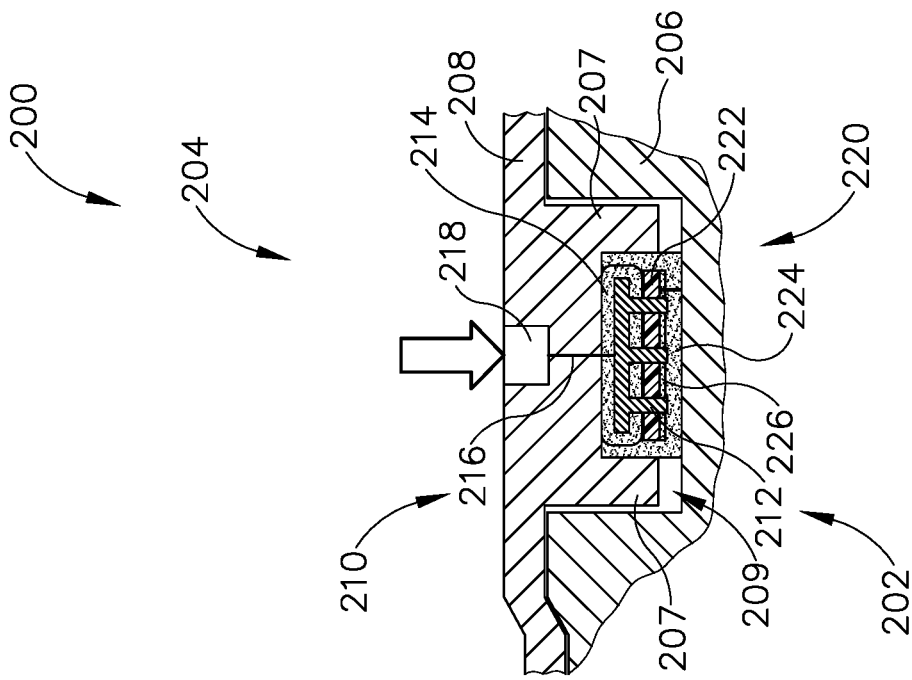
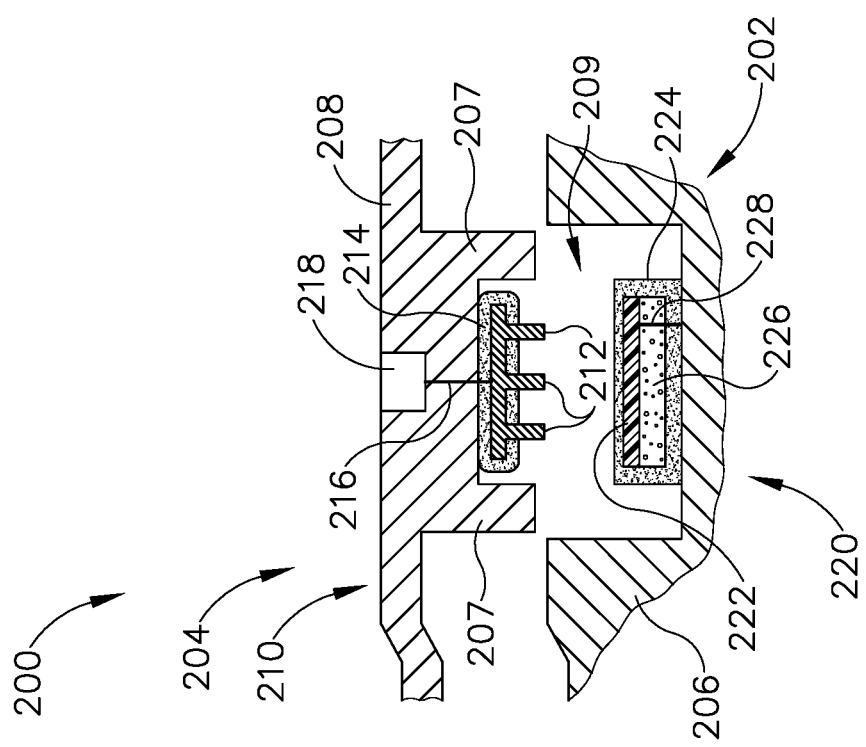

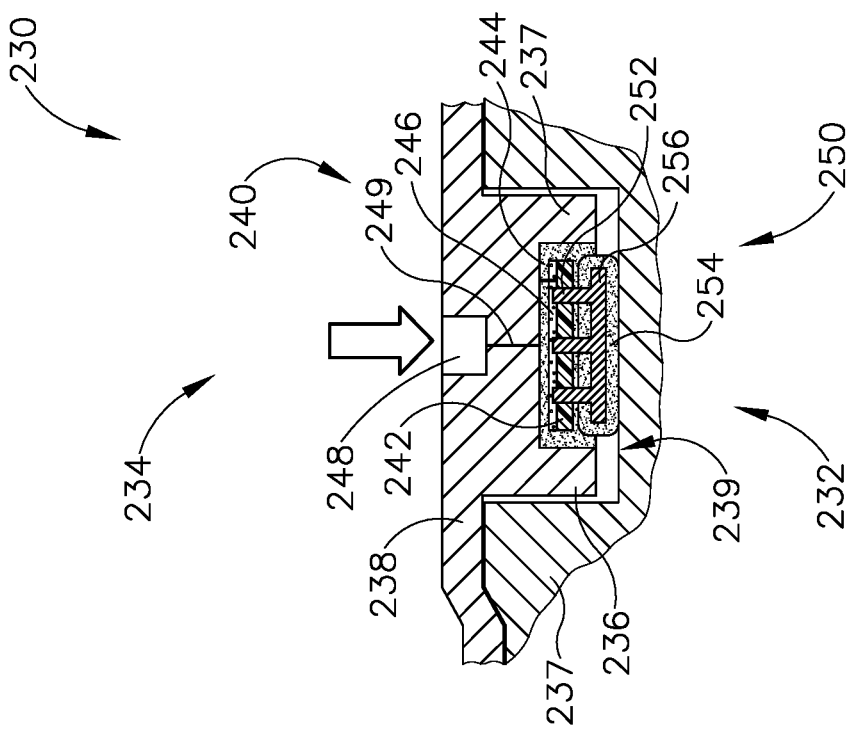
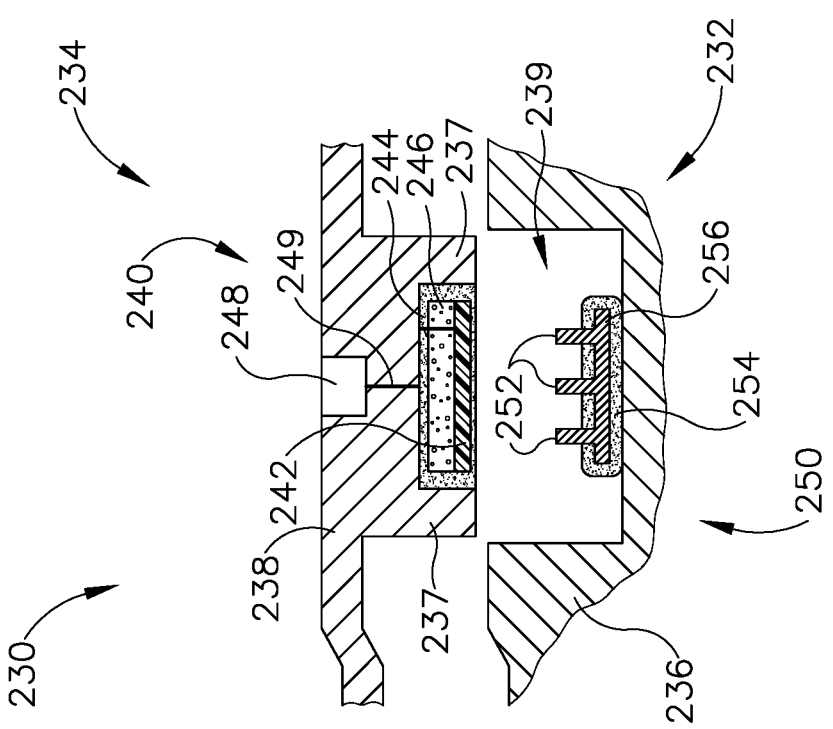

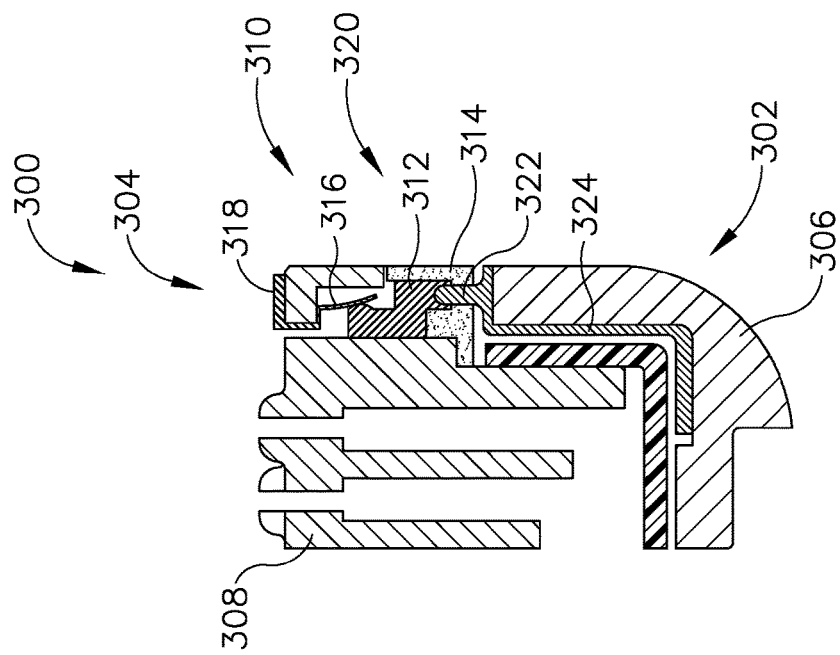
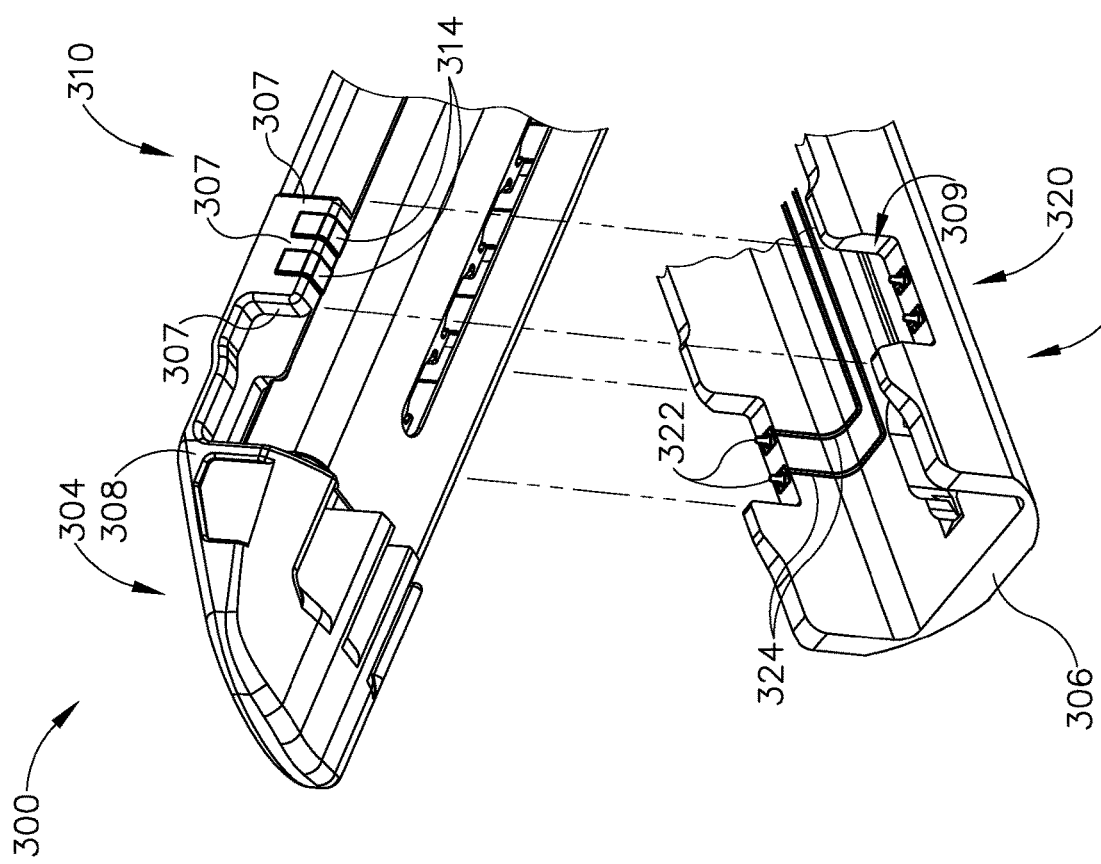

SURGICAL INSTRUMENT WITH ELECTRICAL CONTACT UNDER MEMBRANE

BACKGROUND

Endoscopic surgical instruments may be preferred over traditional open surgical devices in certain instances to create a smaller surgical incision in the patient and thereby reduce the post-operative recovery time and complications. Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,404,508, entitled "Surgical Stapling and Cutting Device," issued Jul. 29, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; U.S. Pat. No. 8,453,914, entitled "Motor-Driven Surgical Cutting Instrument with Electric Actuator Directional Control Assembly," issued Jun. 4, 2013; U.S. Pat. No. 9,186,142, entitled "Surgical Instrument End Effector Articulation Drive with Pinion and Opposing Racks," issued Nov. 17, 2015; and U.S. Pat. No. 9,795,379, entitled "Surgical Instrument with Multi-Diameter Shaft," issued Oct. 24, 2017. The disclosure of each of the above-cited U.S. patents is incorporated by reference herein.

While the surgical staplers referred to above are described as being used in endoscopic procedures, such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Of course, surgical staplers may be used in various other settings and procedures.

While several surgical instruments and systems have been made and used, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 9A depicts a cross-sectional view of an alternative cartridge and channel assembly that may be readily incorporated into the end effector of FIG. 8, where the cartridge is decoupled from the channel;

FIG. 9B depicts a cross-sectional view of the cartridge and channel assembly of FIG. 9A, where the cartridge is coupled with the channel;

FIG. 10A depicts a cross-sectional view of an alternative cartridge and channel assembly that may be readily incorporated into the end effector of FIG. 8, where the cartridge is decoupled from the channel;

FIG. 10B depicts a cross-sectional view of the cartridge and channel assembly of FIG. 10A, where the cartridge is coupled with the channel;

FIG. 12 depicts a perspective view of a distal end of an alternative cartridge and channel assembly that may be readily incorporated into the end effector of FIG. 8, where the cartridge is decoupled from the channel;

FIG. 13 depicts a cross-sectional end view of a portion of the cartridge and channel assembly of FIG. 12, where the cartridge is coupled with the channel;

Figure 1:
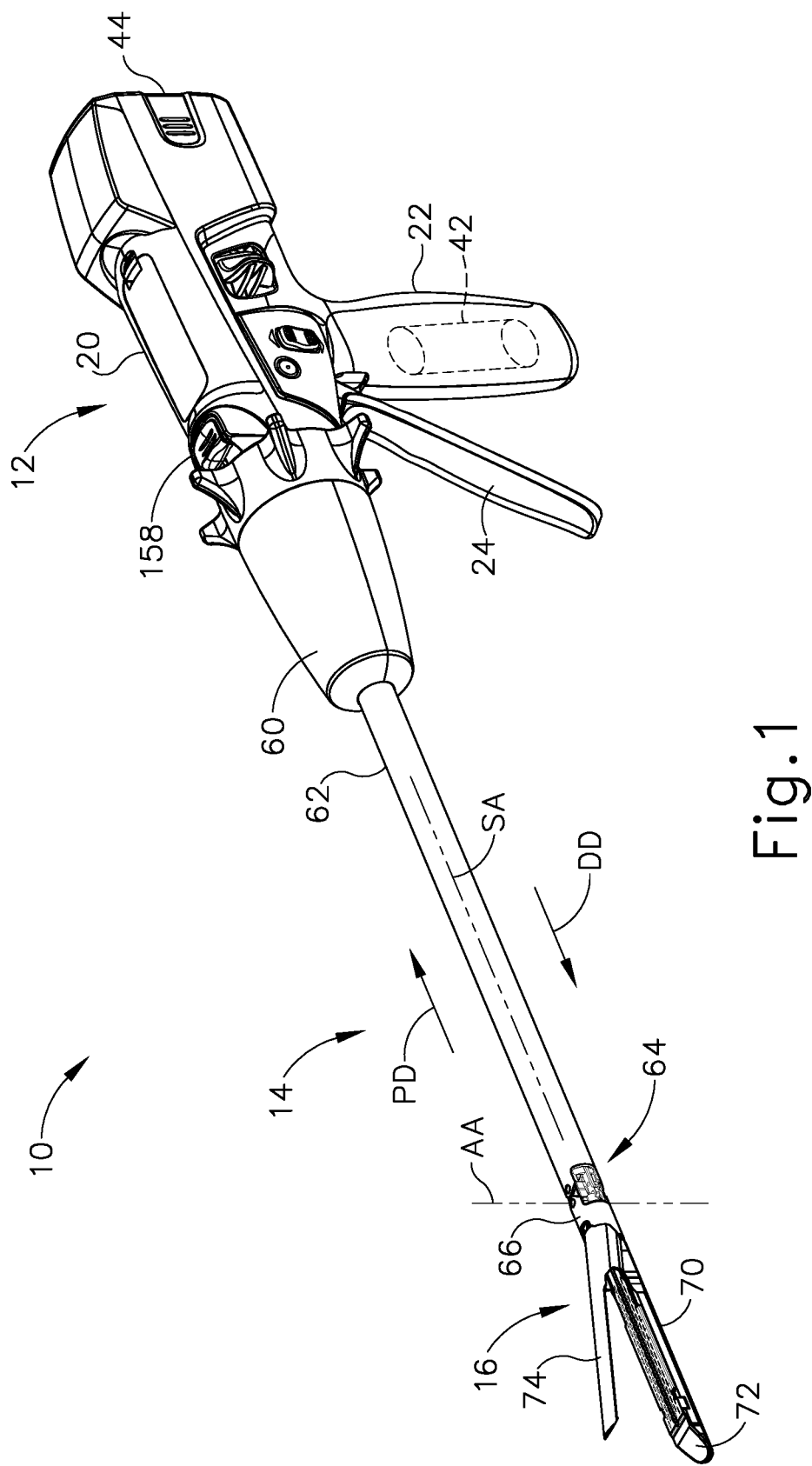
FIG. 1 depicts a perspective view of an exemplary surgical instrument having a handle assembly and an interchangeable shaft assembly.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, clinician, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. EXEMPLARY SURGICAL STAPLING INSTRUMENT

Figure 2:
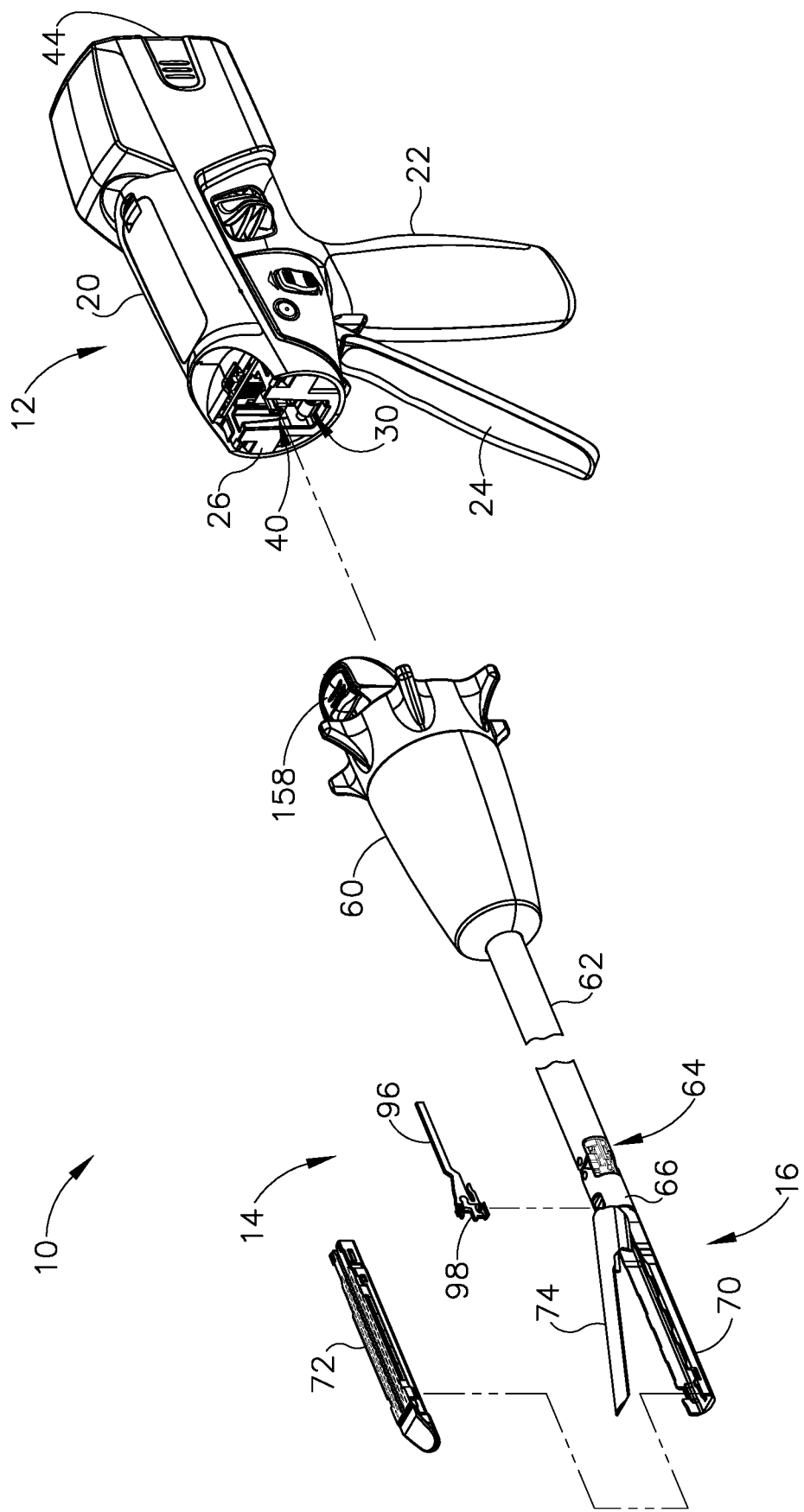
FIG. 2 depicts a partially exploded perspective view of the surgical instrument of FIG. 1, showing the interchangeable shaft assembly separated from the handle assembly.

FIGS. 1-2 show a motor-driven surgical instrument (10) suitable for use in a variety of surgical procedures. In the illustrated example, instrument (10) includes a handle assembly (12) and an interchangeable shaft assembly (14) releasably coupled to and extending distally from handle assembly (12). Interchangeable shaft assembly (14) includes a surgical end effector (16) arranged at a distal end thereof, and which is configured to perform one or more surgical tasks or procedures. In some applications, interchangeable shaft assembly (14) may be effectively employed with a tool drive assembly of a robotically controlled or automated surgical system. For example, interchangeable shaft assembly (14) may be employed with various robotic systems, instruments, components, and methods such as those disclosed in U.S. Pat. No. 9,072,535, entitled "Surgical Stapling Instruments With Rotatable Staple Deployment Arrangements," issued Jul. 7, 2015, the disclosure of which is incorporated by reference herein.

A. Handle Assembly of Surgical Stapling Instrument

Handle assembly (12) comprises a body (20) that includes a pistol grip (22) configured to be grasped by a clinician, and a closure trigger (24) configured to pivot toward and away from pistol grip (22) to selectively close and open end effector (16), as described in greater detail below. In the present example, end effector (16) is configured to cut and staple tissue captured by end effector (16). In other examples, end effector (16) may be configured to treat tissue via application of various other types of movements and energies, such as radio frequency (RF) energy and/or ultrasonic energy, for example.

Figure 3A:
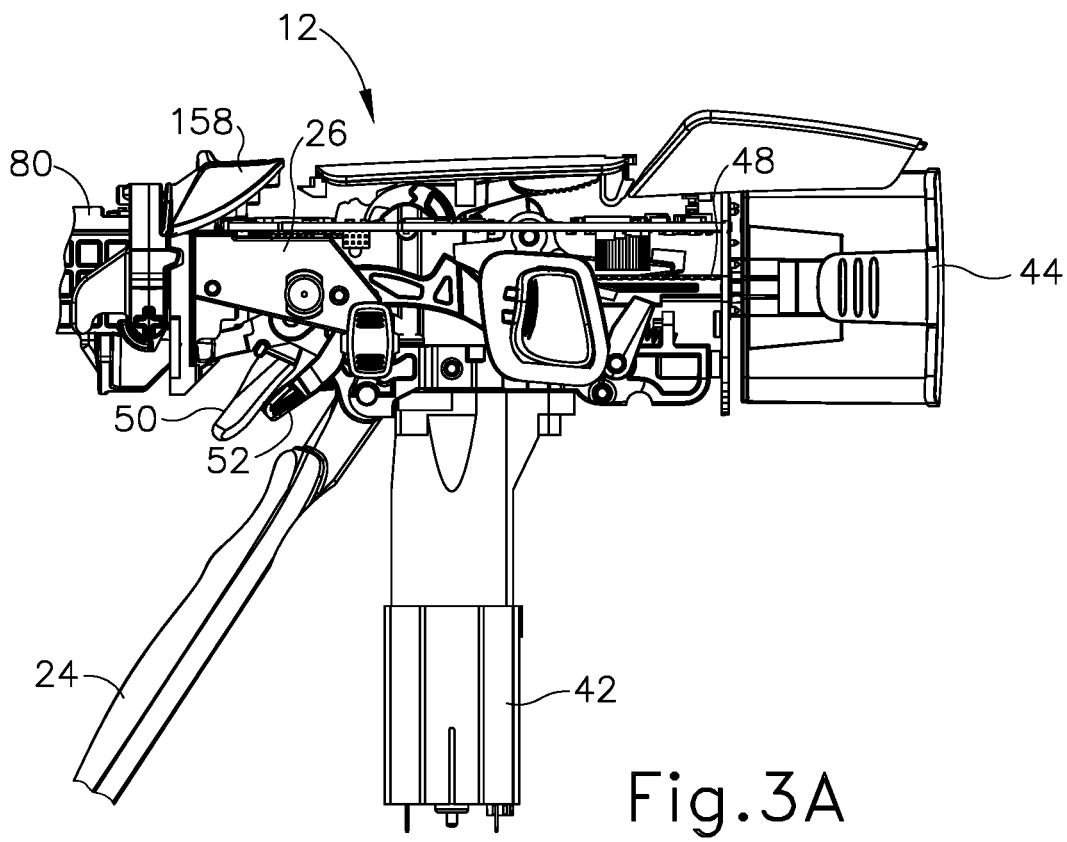
FIG. 3A depicts a side elevational view of the surgical instrument of FIG. 1, with a body of the handle assembly omitted, showing a closure trigger of the handle assembly in an unactuated position.
Figure 3B:
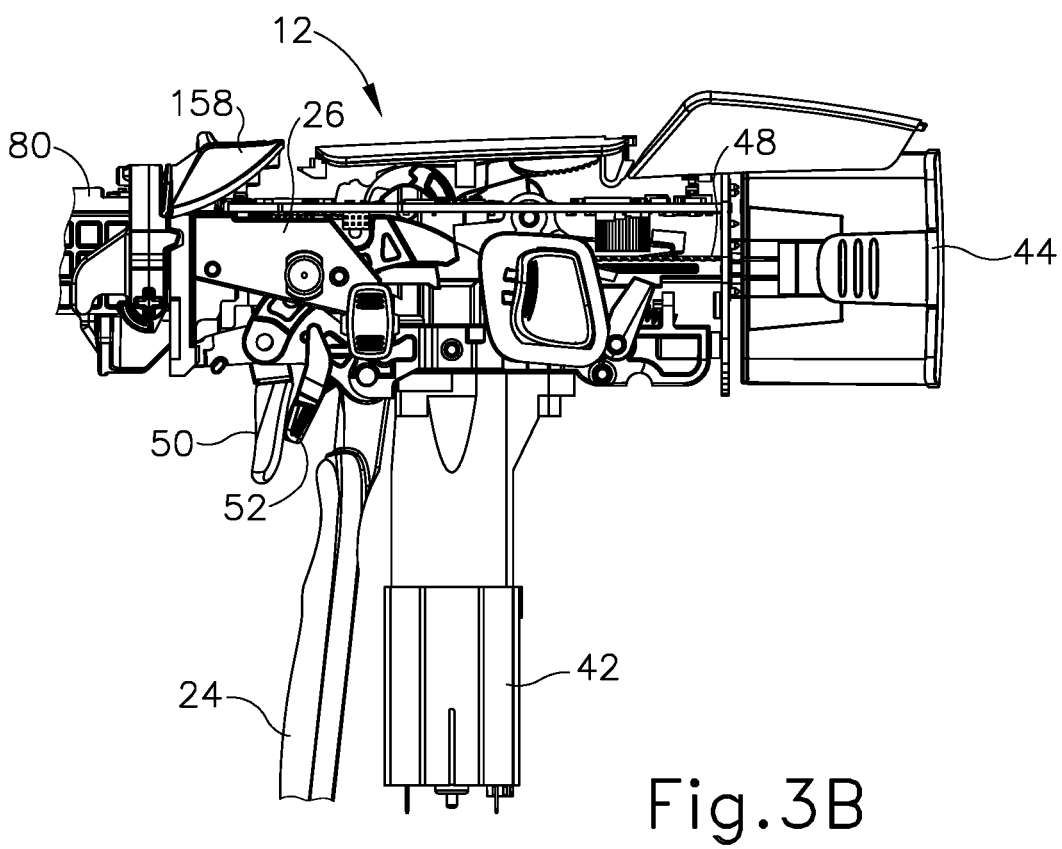
FIG. 3B depicts a side elevational view of the surgical instrument of FIG. 1, with a body of the handle assembly omitted, showing a closure trigger of the handle assembly in an actuated position.
Figure 4:
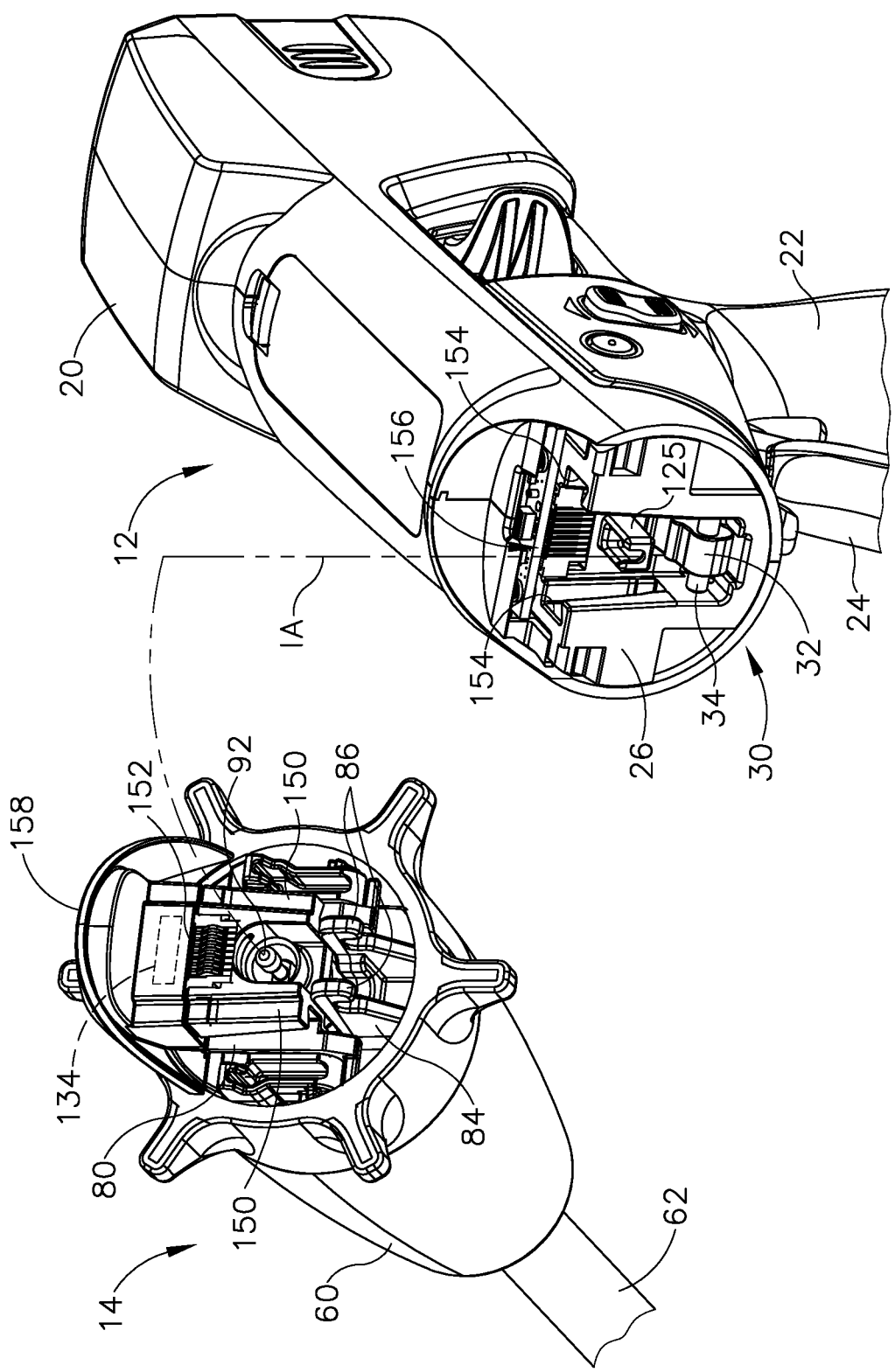
FIG. 4 depicts another perspective view of the surgical instrument of FIG. 1 in a separated state, showing additional details of a distal end of the handle assembly and a mating proximal end of the interchangeable shaft assembly.

As seen in FIGS. 2-4, handle assembly body (20) houses a support structure in the form of a handle frame (26) that supports a plurality of drive systems configured to generate and apply various control motions to corresponding portions of interchangeable shaft assembly (14). In particular, handle frame (26) supports a first drive system in the form of a closure drive system (30) that is operable to selectively close and open end effector (16) to thereby capture and release tissue. Closure drive system (30) includes an actuator in the form of closure trigger (24), which is pivotally supported by handle frame (26) and is operatively coupled with end effector (16) via components of shaft assembly (14) described below. Closure trigger (24) is configured to be squeezed by a clinician toward pistol grip (22) from an unactuated position (FIG. 3A) that provides end effector (16) in an open state for releasing tissue, to an actuated position (FIG. 3B) that provides end effector (16) in a closed state for clamping tissue. Closure trigger (24) may be biased toward the unactuated position by a resilient member (not shown). As seen best in FIG. 4, closure drive system (30) further comprises a linkage assembly that couples closure trigger (24) with end effector (16). The linkage assembly includes a closure link (32) and a transversely extending attachment pin (34) coupled to a distal end of closure link (32). Attachment pin (34) and the distal end of closure link (32) are accessible through a distal opening in handle assembly (12).

Handle assembly body (20) further supports a second drive system in the form of a firing drive system (40) configured to apply firing motions to corresponding portions of interchangeable shaft assembly (14) and its end effector (16). In the present example, firing drive system (40) employs an electric motor (42) that is housed within pistol grip (22) of handle assembly (12) and is operatively coupled with end effector (16), as described below. Electric motor (42) may be of any suitable type, such as a DC brushed motor, a brushless motor, a cordless motor, a synchronous motor, a stepper motor, or any other suitable type of electric motor. Electric motor (42) is powered by a power source shown in the form of a power pack (44) removably coupled to a proximal portion of handle assembly body (20). Power pack (44) includes one or more batteries (not shown) of any suitable type, and may be rechargeable or replaceable.

As seen in FIG. 4, electric motor (42) is electrically coupled to and controlled by a circuit board (46) supported by handle frame (26) within handle assembly body (20). Circuit board (46) may include a microcontroller and is configured to direct power from power pack (44) to electric motor (42) and thereby energize motor (42) to fire end effector (16). Electric motor (42) is configured to interface with a drive gear arrangement (not shown) that is operable to actuate an elongate drive member (48) axially relative to handle frame (26) in response to activation of motor (42). As seen best in FIG. 5, a distal end of drive member (48) is exposed through a distal opening of handle assembly (12) and is configured to couple to a translating member of shaft assembly (14) to thereby operatively couple motor (42) with end effector (16), as described below.

Electric motor (42) is energized by battery pack (44) in response to actuation of a firing trigger (50), which is pivotally supported by handle assembly (12) as best seen in FIGS. 3A and 3B. In the present example, firing trigger (50) is positioned "outboard" of closure trigger (24). Similar to closure trigger (24), firing trigger (50) is configured to be squeezed by the clinician toward pistol grip (22) from an unactuated position (FIG. 3B) to an actuated position (not shown). Firing trigger (50) may be biased toward the unactuated position by a resilient member (not shown). When firing trigger (50) is depressed from the unactuated position to the actuated position, firing trigger (50) causes battery pack (44) to energize motor (42) to actuate drive member (48) longitudinally and thereby fire end effector (16). As shown in FIGS. 3A and 3B, handle assembly (12) further includes a firing trigger safety button (52) that is selectively pivotable between a safety position and a firing position to prevent inadvertent actuation of firing trigger (50).

Figure 5:
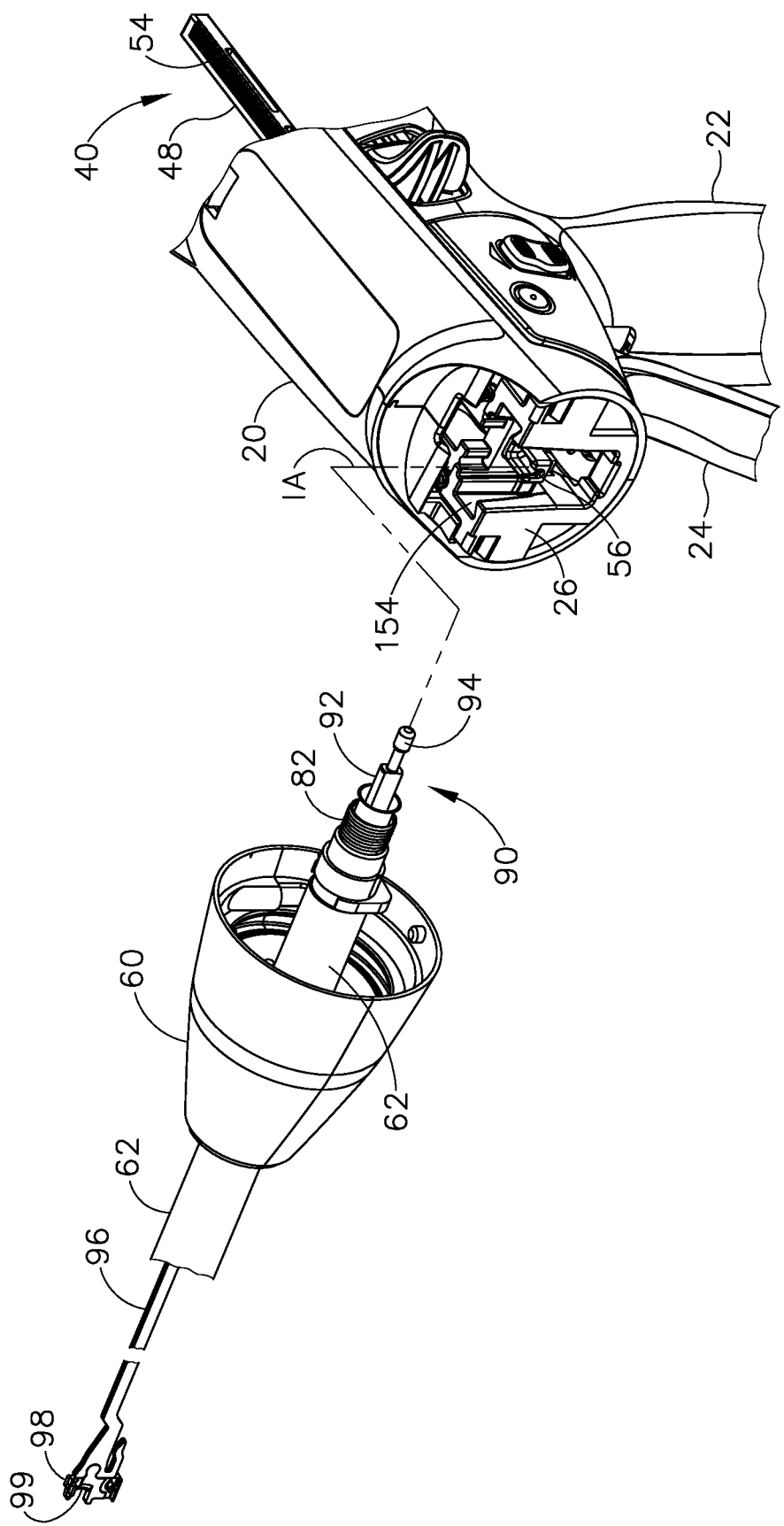
FIG. 5 depicts another perspective view of the surgical instrument of FIG. 1 in a separated state, with certain components of the handle assembly and the shaft assembly omitted to reveal components of a firing system.

As shown best in FIG. 5, elongate drive member (48) of firing drive system (40) includes a rack of teeth (54) formed on at least a proximal portion thereof for meshing engagement with a corresponding drive gear arrangement (not shown) that interfaces with electric motor (42). Drive member (48) further includes an attachment cradle (56) on a distal end thereof, which is configured to receive and couple with an elongate translating member of shaft assembly (14), described below. Drive member (48) is configured to be driven by motor (42) from a proximal position to a distal position to thereby actuate the translating member of shaft assembly (14) and fire end effector (16).

B. Interchangeable Shaft Assembly of Surgical Stapling Instrument

As shown in FIGS. 1-2, interchangeable shaft assembly (14) of the present example includes a proximal nozzle (60), an elongate proximal closure tube (62) extending distally from nozzle (60), an articulation joint (64) disposed at a distal end of the closure tube (62), a distal closure tube segment (66) coupled to a distal end of articulation joint (64), and end effector (16) extending distally therefrom.

End effector (16) includes a first jaw comprising an elongate channel (70) that receives a cartridge (72), and a second jaw comprising an anvil (74) configured to pivot relative to channel (70) between open and closed positions for clamping tissue between anvil (74) and cartridge (72). Cartridge (72) is shown in the form of a conventional staple cartridge having features described in greater detail below, and is configured to fire a plurality of staples into tissue clamped by end effector (16). In other examples, end effector (16) may be suitably configured to apply a variety of other types of motions and energies to tissue captured by end effector (16), such as radio frequency (RF) energy and/or ultrasonic energy, for example. For instance, cartridge (72) may be configured to apply RF to tissue as generally disclosed in U.S. application Ser. No. 15/636,096, entitled "Surgical System Couplable With Staple Cartridge And Radio Frequency Cartridge, And Method Of Using Same," filed Jun. 28, 2017, the disclosure of which is incorporated by reference herein.

Anvil (74) of end effector (16) is operatively coupled with closure drive system (30) of handle assembly (12), and is configured to pivot between open and closed positions, about a pivot axis that extends transversely to shaft axis (SA), in response to actuation of closure trigger (24). In particular, anvil (74) is configured to as assume an open position when closure trigger (24) is in the unactuated position, and a closed position when closure trigger (24) depressed to the actuated position. Anvil (74) is coupled with closure drive system (30) via proximal closure tube (62) and distal closure tube segment (66), among other components described below. Proximal closure tube (62) and distal closure tube segment (66) are configured to translate proximally and distally relative to nozzle (60) to thereby actuate anvil (74) about its pivot axis in response to actuation of closure trigger (24).

Articulation joint (64) is configured to provide articulation of end effector (16) relative to proximal closure tube (62) and corresponding components of shaft assembly (14) about an articulation axis (AA) that extends transversely to shaft axis (SA). In some examples, end effector (16) may be articulated to a desired orientation by pushing end effector (16) against soft tissue and/or bone within the patient. In other examples, end effector (16) may be articulated by an articulation driver (not shown).

As best seen in FIG. 4, nozzle (60) of interchangeable shaft assembly (14) houses a support structure in the form of a tool chassis (80) that rotatably supports nozzle (60). Nozzle (60) and end effector (16) are configured to rotate relative to tool chassis (80) about shaft axis (SA), as indicated in FIG. 1. As shown in FIG. 5, proximal closure tube (62) houses an internal spine (82) that is rotatably supported by tool chassis (80) (omitted from view in FIG. 5) at a proximal end and is coupled to end effector (16) at a distal end. Tool chassis (80) further supports a closure shuttle (84) that is configured to translate proximally and distally relative to tool chassis (80). A distal end of closure shuttle (84) is coupled to and rotatably supports a proximal end of proximal closure tube (62). A proximal end of closure shuttle (84) includes a pair of proximally extending hooks (86) configured to couple with closure drive system (30) of handle assembly (12). In particular, hooks (86) are configured to releasably capture attachment pin (34) of closure drive system (30) when interchangeable shaft assembly (14) is coupled with handle assembly (12). Accordingly, actuation of closure trigger (24) to the actuated position (see FIG. 3B) drives closure shuttle (84) distally, which in turn drives proximal closure tube (62) and distal closure tube segment (66) distally, thereby actuating anvil (74) to a closed position for clamping tissue with end effector (16). Returning trigger to the unactuated position (see FIG. 3A) actuates these components proximally, thereby returning anvil (74) to an open position.

As seen best in FIG. 5, interchangeable shaft assembly (14) further includes an internal firing system (90) configured to operatively couple with firing drive system (40) of handle assembly (12) when shaft assembly (14) is coupled to handle assembly (12). Firing system (90) includes an intermediate firing shaft (92) slidably received within spine (82) and proximal closure tube (62). Intermediate firing shaft (92) includes a proximal end having an attachment lug (94) configured to rotatably seat within attachment cradle (56) of drive member (48) of firing drive system (40), and a distal end configured to couple to an elongate knife bar (96). Knife bar (96) is connected at its distal end to a knife member (98), which includes a sharpened cutting edge (99) configured to sever tissue clamped by end effector (16) as knife member advances distally through staple cartridge (72). Accordingly, actuation of firing trigger (50) actuates drive member (48) distally, which in turn drives intermediate firing shaft (92), knife bar (96), and knife member (98) distally to thereby cut tissue and simultaneously fire staple cartridge (72), as described below. Knife member (98) may include one or more anvil engagement features configured to engage and maintain anvil (74) in a closed state throughout cutting and stapling of tissue.

Figure 6:
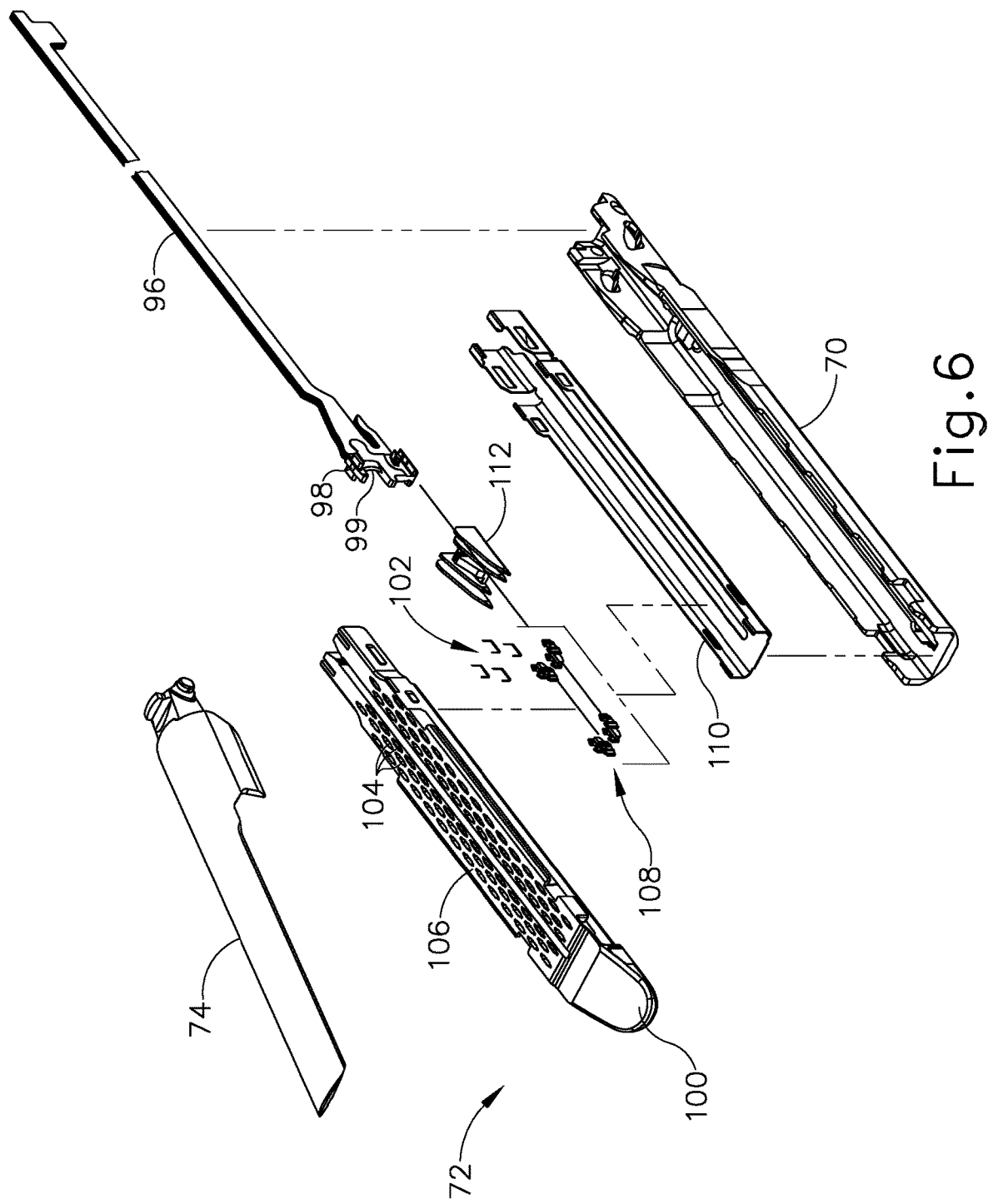
FIG. 6 depicts an exploded perspective view of an end effector of the surgical instrument of FIG. 1, in combination with certain components of the firing system.

As seen best in FIG. 6, staple cartridge (72) includes a molded cartridge body (100) that houses a plurality of staples (102) within staple cavities (104) that open upwardly through a staple deck (106) of cartridge body (100). A plurality of staple drivers (108) are positioned within staple cavities (104), beneath staples (102). A cartridge tray (110) covers an open bottom side of cartridge body (100) and holds together the various components of staple cartridge (72). A wedge sled (112) is slidably received within slots formed in cartridge body (100), and is driven distally by knife member (98) upon actuation of firing drive system (40). As wedge sled (112) advances distally through staple cartridge (72), wedge sled (112) cams staple drivers (108) upwardly to thereby drive staples (102) through tissue clamped by anvil (74) and into staple forming pockets (not shown) formed in anvil (74), thereby deforming staples (102). Simultaneously, cutting edge (99) of knife member (98) severs the tissue clamped in end effector (16). After firing staple cartridge (72), knife member (98) may be retracted to a proximal position to thereby permit opening of anvil (74) and release of the stapled/severed tissue.

C. Electrical Connections Within Surgical Instrument

Interchangeable shaft assembly (14) and variations thereof that are suitable for use with handle assembly (12) may employ one or more sensors and/or various other electrical components that require electrical communication with handle circuit board (46) of handle assembly (12). For instance, a proximal portion of shaft assembly (14) and/or end effector (16) may include one more sensors (see e.g., FIG. 8) and/or one or more RF electrodes (not shown) configured to electrically couple with handle circuit board (46) to enable operation thereof. As described below, shaft assembly (14) is suitably configured to enable rotation of end effector (16), among other components of shaft assembly (14), relative to handle assembly (12) while maintaining electrical coupling between shaft assembly (14) and handle assembly (12).

Figure 7:
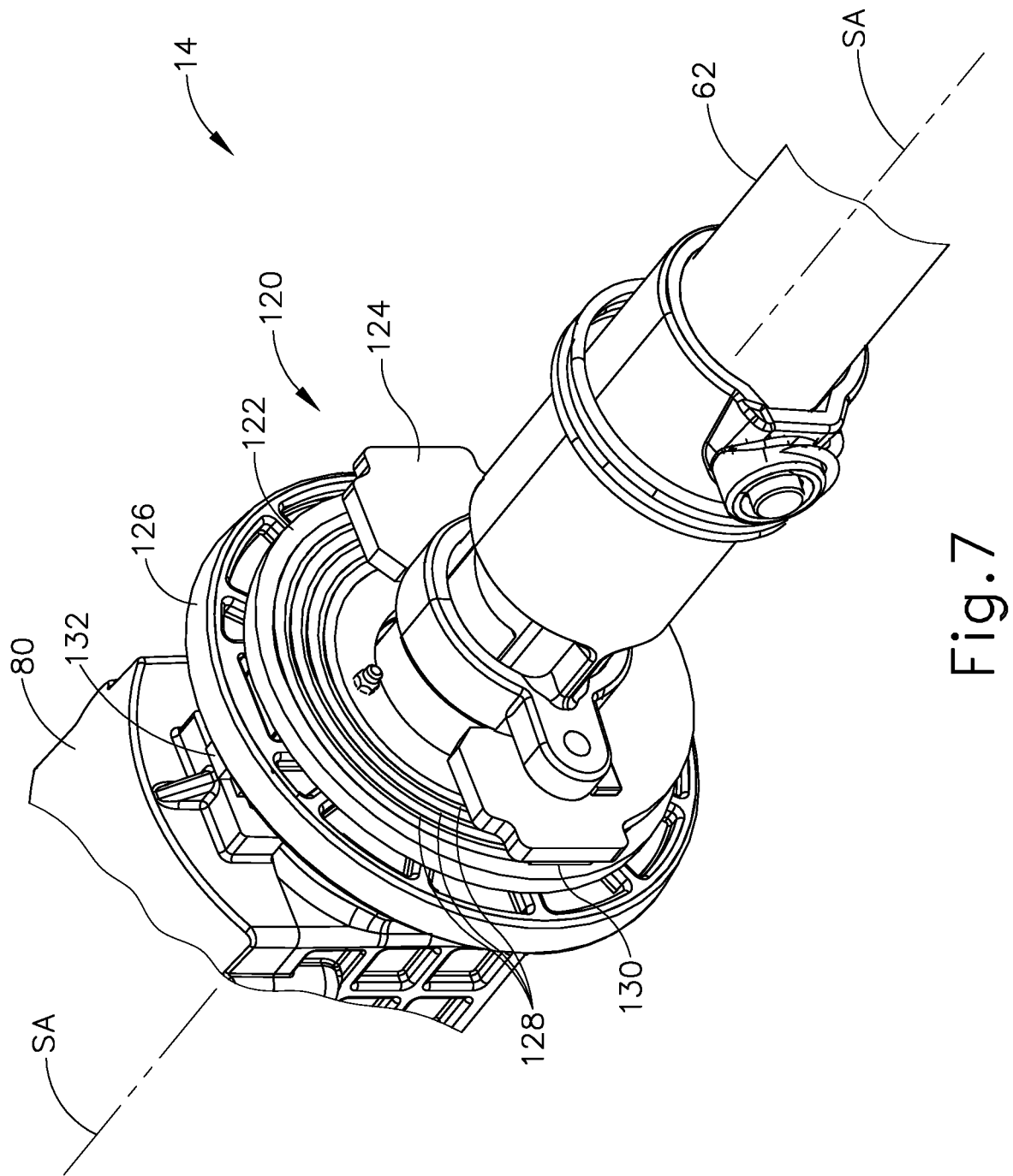
FIG. 7 depicts a perspective view of a proximal portion of the interchangeable shaft assembly of the surgical instrument of FIG. 1, with a nozzle of the shaft assembly omitted to reveal details of an internal slip ring assembly.

As shown in FIG. 7, interchangeable shaft assembly (14) further includes a slip ring assembly (120) housed within nozzle (60) and configured to electrically couple shaft assembly (14) with handle assembly (12) for communication of electrical power and/or sensor signals between end effector (16) and handle circuit board (46). Slip ring assembly (120) is configured to provide such electrical communication while facilitating rotation of nozzle (60) and end effector (16), among other rotating components of shaft assembly (14), relative to tool chassis (80) and handle assembly (12) about shaft axis (SA). Slip ring assembly (120) comprises a proximal connector flange (122) mounted to a chassis flange (126) that extends distally from tool chassis (80), and a distal connector flange (124) secured to an interior of nozzle (60). Distal connector flange (124) is configured to rotate with nozzle (60) relative to tool chassis (80) and chassis flange (126). Accordingly, the proximal face of distal connector flange (124) confronts and is configured to rotate relative to a distal face of proximal connector flange (122) about shaft axis (SA).

The distal face of proximal connector flange (122) of slip ring assembly (120) includes a plurality of annular conductors (128) arranged substantially concentrically. The proximal face of distal connector flange (124) supports one or more electrical coupling members (130) each supporting a plurality of electrical contacts (not shown). Each electrical contact is positioned to contact a respective annular conductor (128) of proximal connector flange (122). Such an arrangement permits relative rotation between proximal connector flange (122) and distal connector flange (124) while maintaining electrical contact therebetween. Proximal connector flange (122) includes an electrical connector (132) extending proximally from a proximal face of proximal connector flange (122). Electrical connector (132) is configured to electrically couple annular conductors (128) with a shaft circuit board (134), shown schematically in FIG. 4, which may be mounted to shaft chassis (80) and include a microcontroller.

D. Attachment of Interchangeable Shaft Assembly to Handle Assembly

As described in greater detail below, interchangeable shaft assembly (14) is configured to be releasably coupled with handle assembly (12). It will be appreciated that various other types of interchangeable shaft assemblies having end effectors configured for various types of surgical procedures may be used in combination with handle assembly (12) described above.

As shown best in FIG. 4, a proximal end of tool chassis (80) of interchangeable shaft assembly (14) includes a pair of tapered attachment members (150) extending transversely to shaft axis (SA), and a shaft-side electrical connector (152) positioned therebetween. Shaft electrical connector (152) is in electrical communication with shaft circuit board (134) of shaft assembly (14). A distal end of handle frame (26) of handle assembly (12) includes a pair of dovetail receiving slots (154), and a handle-side electrical connector (156) arranged therebetween. Handle electrical connector (156) is in electrical communication with handle circuit board (46)

of handle assembly (12). During attachment of shaft assembly (14) to handle assembly (12), as described below, tapered attachment members (150) are received within dovetail receiving slots (154) along an installation axis (IA) that is transverse to shaft axis (SA). Additionally, shaft electrical connector (152) is electrically coupled with handle electrical connector (156). The proximal end of interchangeable shaft assembly (14) additionally includes a latch assembly (158) configured to releasably latch tool chassis (80) to handle frame (26) of handle assembly (12) when shaft assembly (14) is coupled with handle assembly (12).

As shown in FIG. 4, to attach interchangeable shaft assembly (14) to handle assembly (12), the clinician first aligns tapered attachment members (150) of tool chassis (80) with dovetail receiving slots (154) of handle frame (26). The clinician then moves shaft assembly (14) toward handle assembly (12) along installation axis (IA), thereby seating tapered attachment members (150) within dovetail receiving slots (154) and lockingly engaging latch assembly (158) with a distal portion of handle assembly (12). In doing so, attachment lug (94) of intermediate firing shaft (92) is also seated within cradle (56) of longitudinally movable drive member (48), thereby operatively coupling firing system (90) of shaft assembly (14) with firing drive system (40) of handle assembly (12). Additionally, proximal hooks (86) of closure shuttle (84) slide over and capture opposed lateral ends of attachment pin (34) extending from closure link (32), thereby operatively coupling the anvil closure components of shaft assembly (14) with closure drive system (30) of handle assembly (12). Additionally, during attachment of shaft assembly (14) with handle assembly (12), shaft electrical connector (152) on tool chassis (80) is electrically coupled with handle electrical connector (156) on handle frame (26), thereby placing shaft circuit board (134) of shaft assembly (14) in electrical communication with handle circuit board (46) of handle assembly (12).

In various examples, surgical instrument (10) may be further configured in accordance with one or more teachings of U.S. Pat. No. 9,345,481, entitled "Staple Cartridge Tissue Thickness Sensor System," issued May 24, 2016; U.S. Pat. No. 8,608,045, entitled "Powered Surgical Cutting and Stapling Apparatus With Manually Retractable Firing System," issued Dec. 17, 2013; U.S. application Ser. No. 15/635,631, entitled "Method For Articulating A Surgical Instrument," filed Jun. 28, 2017; U.S. application Ser. No. 15/635,631, entitled "Surgical Instrument With Axially Moveable Closure Member," filed Jun. 28, 2017; U.S. application Ser. No. 15/635,837, entitled "Surgical Instrument Comprising An Articulation System Lockable To A Frame," filed Jun. 28, 2017; U.S. Pat. Pub. No. 2016/0066911, entitled "Smart Cartridge Wake Up Operation And Data Retention," published Mar. 10, 2016; U.S. Pat. Pub. No. 2015/0272575, entitled "Surgical Instrument Comprising A Sensor System," published Oct. 1, 2015; U.S. Pat. Pub. No. 2014/0263552, entitled "Staple Cartridge Tissue Thickness Sensor System," published Sep. 18, 2014; and/or U.S. Pat. Pub. No. 2014/0263541, entitled "Articulatable Surgical Instrument Comprising An Articulation Lock," published Sep. 18, 2014, the disclosures of which are incorporated by reference herein.

E. Exemplary End Effector With Sensors

In some instances, it may be desirable to provide the end effector of a surgical instrument with one or more sensors for sensing various operating conditions of the end effector. Such sensed conditions can then be communicated as electrical signals to a controller of the surgical instrument, such as a controller of shaft circuit board (134) and/or handle circuit board (46) of instrument (10) described above. The controller(s) may then take one or more actions in response to receiving such signals, such as providing one or more indications to the clinician operating the instrument.

Figure 8:
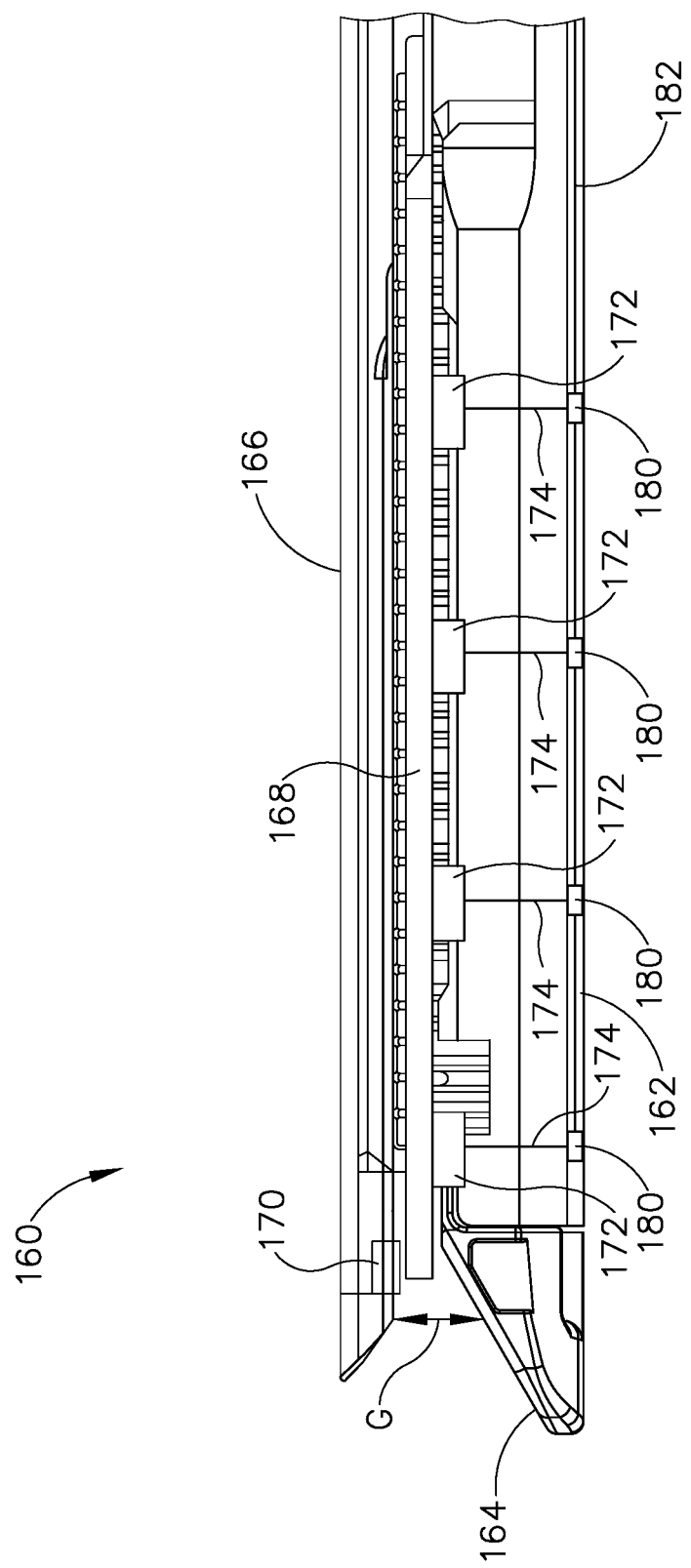
FIG. 8 depicts a side elevational view of another exemplary end effector having a plurality of sensors.

FIG. 8 illustrates an exemplary alternative end effector (160) suitable for use with surgical instrument (10) described above. End effector (160) is similar to end effector (16) described above in that end effector (160) includes a first jaw comprising an elongate channel (162) that receives a staple cartridge (164), and a second jaw comprising an anvil (166) configured to pivot relative to channel (162) between open and closed positions for clamping tissue (168) between anvil (166) and staple cartridge (164). Staple cartridge (164) may be similar to staple cartridge (72) described above.

End effector (160) differs from end effector (16) in that end effector (160) includes a first sensor (170) disposed on a tissue clamping side of anvil (166), and a plurality of second sensors (172) spaced along a length of staple cartridge (164). In other versions, one or more sensors, such as one or more of second sensors (172), may be provided on staple channel (162). In the present example, first sensor (170) is configured to detect one or more conditions of end effector (160), such as a gap (G) between anvil (166) and staple cartridge (164), which may correspond to a thickness of tissue (168) clamped by end effector (160). Second sensors (172) are also configured to detect one or more conditions of end effector (160) and/or of tissue (168) clamped by end effector (160). For instance, second sensors (172) may be configured to detect one or more conditions such as a color of staple cartridge (164), a length of staple cartridge (164), a clamping condition of end effector (160), and/or the number of actual and/or remaining uses of end effector (160) and/or staple cartridge (164), for example. While end effector (160) is shown having one first sensor (160) and four second sensors (172), various other suitable quantities and arrangements of sensors (170, 172) may be provided in other examples.

Each sensor (170, 172) may comprise any sensor type suitable for measuring the respective one or more conditions of end effector (160). For instance, each sensor (170, 172) may comprise a magnetic sensor (e.g., a Hall effect sensor), a strain gauge, a pressure sensor, an inductive sensor (e.g., an eddy current sensor), a resistive sensor, a capacitive sensor, or an optical sensor, for example. Each sensor (170, 172) is configured to communicate electrical signals corresponding to a sensed condition of end effector (160) to shaft circuit board (134), which may in turn communicate information based on the signals to handle circuit board (46), via slip ring assembly (120) described above.

It should be understood that channel (162) may selectively receive staple cartridge (164) such that staple cartridge (164) may be attached to channel (162), used in accordance with the description herein, removed from channel (162), and replaced with an unused, second staple cartridge (164). Therefore, sensors (172) associated with staple cartridge (164) may be configured to selectively establish an electrical connection with shaft circuit board (134) once staple cartridge (164) is suitably coupled to channel (162). In the current example, second sensors (172) each include an electrical contact (174), while channel (162) includes a plurality of electrical contacts (180). Corresponding contacts (174, 180) are dimensioned to electrically couple with each other when staple cartridge (164) is suitably coupled with channel (162). Additionally, channel (162) includes electrical traces (182) extending from contacts (180) all the way to electrical coupling member (130)

of slip ring assembly (120). Therefore, when staple cartridge (164) is suitably coupled with channel (162), second sensors (172) are in electrical communication with shaft circuit board (134).

While sensors (172) are attached to staple cartridge (164) in the present example, any other type of electrically activated components may be used in addition to, or in replacement of, sensors (172). For example, one or more sensors (172) may be replaced with one or more elements designed to deliver electrical therapeutic energy to tissue captured within end effector (160), such as a pad that transmits Radio Frequency (RF) energy to tissue.

II. ALTERNATIVE CARTRIDGE AND CHANNEL ASSEMBLIES WITH ALTERNATIVE ELECTRICAL CONTACTS

As mentioned above, second sensors (172) associated with staple cartridge (164) are configured to couple with shaft circuit board (134) via contacts (174, 180) and electrical tracing (182) when staple cartridge (164) is suitably coupled with channel (162). As also mentioned above, shaft circuit board (134) may be powered by power pack (44) when interchangeable shaft assembly (14) is suitably coupled with handle assembly (12) in accordance with the description above. Therefore, when handle assembly (12) and interchangeable shaft assembly (14) are suitably coupled while power pack (44) is powering handle assembly (12), power pack (44) is also in electrical communication with contacts (180) located along channel (162).

As also mentioned above, staple cartridge (164) is dimensioned to selectively couple with channel (162) such that a first staple cartridge (164) may be used in accordance with the teachings herein, then be removed from channel (162), and then be replaced with an unused, second staple cartridge (164). Between removing a first staple cartridge (164) from channel (162) and coupling a second staple cartridge (164) with channel (162), an operator may dip the distal end of shaft assembly (14), including channel (162), into a saline solution to clean shaft assembly (14) for another use. Additionally, during exemplary use, bodily fluids may accumulate within channel (162) and cartridge (164). Accumulation of saline solutions or bodily fluids may interfere with the electrical connection between corresponding contacts (174, 180), adversely affecting the electrical connection between corresponding contacts (174, 180). Additionally, Accumulation of saline solutions or bodily fluids may interfere with specific contacts (174, 180) creating an undesirable short circuit.

Therefore, it may be desirable to provide a cartridge, and/or channel assembly that may help prevent undesirable short circuits or other interferences with electrical connections (174, 180) via exposure to various fluids. While various examples of cartridges and channels are described below, it should be understood various combinations or modifications may be made to such cartridges and channels as would be apparent to one having ordinary skill in the art in view of the teachings herein.

A. Cartridges and Channels with Stationary Electrical Couplings having Membranes FIGS. 9A-9B show an exemplary alternative cartridge and channel assembly (200) that may be readily incorporated into end effector (160) in replacement of cartridge (164) and channel (162), as described above, respectively. Cartridge and channel assembly (200) include an elongate channel (202) and a staple cartridge (204). Channel (202) and cartridge (204) are substantially similar to channel (162) and cartridge (164) as described above, respectively, with differences elaborated below. In particular, FIG. 9A shows cartridge (204) decoupled from channel (202); while FIG. 9B shows cartridge (204) coupled with channel (202).

Staple cartridge (204) includes a cartridge body (208), and a cartridge contact assembly (210). In the current example, cartridge body (208) includes a laterally extending lug or protrusion (207). Laterally extending lug (207) is dimensioned to fit within recess (209) defined by channel body (206). A portion of cartridge contact assembly (210) is located on the underside of laterally extending lug (207) in order to suitably couple with channel contact assembly (220).

Cartridge contact assembly (210) includes a plurality of sharp contacts (212), an insulative membrane (214), an electrically activated component (218), and a connection extending between sharp contacts (212) and electrically activated component (218). Sharp contacts (212) are configured to electrically couple with contact member (222) when cartridge (204) is suitably coupled with channel (202). In particular, sharp contacts (212) are configured to puncture a membrane (224) in order to electrically couple with contact member (222). When contact member (222) and sharp contacts (212) are electrically coupled, and when handle assembly (12) is suitably coupled with shaft assembly (14), power pack (44) may power electrically activated component (218).

Membrane (214) surrounds a portion of sharp contacts (212). Membrane (214) is formed of a material that prevents fluid from travelling through membrane (214). In other words, membrane (214) acts as a barrier for fluid communication. Membrane (214) may be formed of the same material as membrane (224) described below, or any other suitable material that would be apparent to one having ordinary skill in the art in view of the teachings herein.

Channel (202) includes a channel body (206) defining a recess (209) housing a channel contact assembly (220). In the current example, the portion of channel body (206) defining recess (209) is a side wall, such that the side wall of channel body (206) extends downward to a base, which connects to an opposing side wall that may also define a recess (209). While in the current example, channel (202) only shows a single channel contact assembly (220), any suitable number of channel contact assembly (220) may be utilized as would be apparent to one having ordinary skill in the art in view of the teachings herein. For instance, in examples where there is an opposing side wall, a channel contact assembly (220) may be located within a recess (209) of the opposing wise wall.

Channel contact assembly (220) includes an electrical contact member (222), an insulative membrane (224), a flexible pad (226), and an electrical trace (228). The number of channel contact assemblies (220) may mirror the number of cartridge contact assemblies (210) such that there are corresponding contact assemblies (210, 220). Similar to electrical trace (182) described above, electrical trace (228) extends from electrical contact member (222), through channel (202), and connects with shaft circuit board (134). Therefore, when shaft assembly (14) and handle assembly (12) are suitably coupled while power pack (44) powers handle assembly (12), electrical trace (228) may help provide electrically communication between electrical contact member (222) and power pack (44). While in the current example, electrical trace (228) is used to help establish electrical communication between contact member (222) of channel (202) and power pack (44), any other suitable structure may be used as would be apparent to one having ordinary skill in the art in view of the teachings herein.

Flexible pad (226) and electrical contact member (222) are directly adjacent to each other and housed within insulative membrane (224). Flexible pad (226) may be sufficiently resilient such that flexible pad (226) may deform under pressure, and return to an intended shape when no longer under pressure. The flexible and resilient nature of flexible pad (226) may allow electrical contact member (222) to move within insulative membrane (224). It should be understood that flexible pad (226) is entirely optional and may be omitted.

Electrical contact member (222) is configured to selectively receive a corresponding sharp contact (212) in order to establish electrical communication between channel contact assembly (220) and cartridge contact assembly (210). Electrical contact member (222) may include various components, shapes, or materials as would be apparent to one having ordinary skill in the art in view of the teachings herein.

As mentioned above, insulative membrane (224) houses electrical contact member (222) and flexible pad (226). Insulative membrane (224) may be made from a sufficient material such that membrane (224) may fluidly isolate electrical contact member (222) from the exterior of membrane (224). Therefore, if an exterior portion of membrane (224) is exposed to a fluid, such as bodily fluid or a saline solution, that fluid will not penetrate membrane (224) toward electrical contact member (222). Insulative membrane (224) is also made from a material that may be punctured under sufficient pressure, such as when sharp contacts (212) are pushed against membrane (224) with sufficient force, as described herein. The properties of membrane (224) are also such that when punctured, membrane (224) may also form a seal around the puncture area, such that membrane (224) also resists fluid transfer through the punctured area. In the alternative, insulative membrane (224) may be made of a material the that has an occluded opening that may expand in response to contacts (212) being pressed through membrane (224) such that contact (212) may extend through the opening. Additionally, membrane (224) may be sufficiently elastic that after sharp contacts (212) are removed from membrane (224), such as when cartridge (204) is removed from channel (202), the punctured portion of membrane (224) self-closes around the puncture site to protect electrical contact member (222) from exposure to fluid. As can be seen in FIG. 9B, when sharp contacts (212) are coupled with contact member (222), membranes (214, 224) together form a barrier that may prevent fluid from interfering with the electrical connection between contacts (212, 222).

FIGS. 10A-10B show another exemplary alternative cartridge and channel assembly (230) that may be readily incorporated into end effector (160) in replacement of cartridge (164) and channel (162), as described above, respectively. Cartridge and channel assembly (230) includes an elongate channel (232) and a staple cartridge (234). Cartridge and channel assembly (230) assembly are substantially similar to cartridge and channel assembly (200) described above, except that sharp contacts (252) are now associated with channel (232) and contact member (242) is associated with cartridge (234). FIG. 10A shows cartridge (234) decoupled from channel (202); while FIG. 10B shows cartridge (234) coupled with channel (232).

Channel (232) includes a channel body (236) defining a recess (239), and a channel contact assembly (250). In the current example, the portion of channel body (236) defining recess (239) is a side wall, such that the side wall of channel body (236) extends downward to a base, which connects to an opposing side wall that may also define a recess (239). While in the current example, channel (232) only shows a single channel contact assembly (250), any suitable number of channel contact assemblies (250) may be utilized as would be apparent to one having ordinary skill in the art in view of the teachings herein. For instance, in examples where there is an opposing side wall, a channel contact assembly (250) may be located within a recess (239) of the opposing wise wall.

Channel contact assembly (250) includes a plurality of sharp contacts (252), an insulative membrane (254), and an electrical trace (256). Similar to electrical trace (182) described above, electrical trace (256) extends from sharp contacts (252), through channel (232), and connects with shaft circuit board (134). Therefore, when shaft assembly (14) and handle assembly (12) are suitably coupled while power pack (44) powers handle assembly (12), electrical trace (256) may help provide electrically communication between electrical contact member (252) and power pack (44). While in the current example, electrical trace (256) is used to help establish electrical communication between sharp contacts (252) of channel (232) and power pack (44), any other suitable structure may be used as would be apparent to one having ordinary skill in the art in view of the teachings herein. Sharp contacts (252) are configured to electrically couple with contact member (242) when cartridge (234) is suitably coupled with channel (232). In particular, sharp contacts (232) are configured to puncture a membrane (244) in order to electrically couple with contact member (242). When contact member (242) and sharp contacts (252) are electrically coupled, and when handle assembly (12) is suitably coupled with shaft assembly (14), power pack (44) may power electrically activated component (248).

Membrane (254) surrounds a portion of sharp contacts (252). Membrane (254) is formed of a material that prevents fluid from travelling through membrane (254). In other words, membrane (254) acts as a barrier for fluid communication. Membrane (254) may be formed of the same material as membrane (214) described below, or any other suitable material that would be apparent to one having ordinary skill in the art in view of the teachings herein.

Cartridge (234) includes a cartridge body (238) and a cartridge contact assembly (250). In the current example, cartridge body (238) includes a laterally extending lug or protrusion (237). Laterally extending lug (237) is dimensioned to fit within recess (239) defined by channel body (236). A portion of cartridge contact assembly (250) is located on the underside of laterally extending lug (237) in order to suitably couple with channel contact assembly (250).

Cartridge contact assembly (240) includes an electrical contact member (242), an insulative membrane (244), a flexible pad (246), an electrically activated component (248), and a connection (249) extending between contact member (242) and electrically activated component (248). The number of cartridge contact assemblies (240) may mirror the number of channel contact assemblies (250) such that there are corresponding contact assemblies (240, 250).

Flexible pad (246) and electrical contact member (242) are directly adjacent to each other and housed within insulative membrane (244). Flexible pad (246) may be sufficiently resilient such that flexible pad (246) may deform under pressure, and return to an intended shape when no longer under pressure. The flexible and resilient nature of flexible pad (246) may allow electrical contact member (242) to move within insulative membrane (244). It should be understood that flexible pad (246) is entirely optional and may be omitted.

Electrical contact member (242) is configured to selectively receive a corresponding sharp contact (252) in order to establish electrical communication between channel contact assembly (250) and cartridge contact assembly (240). Electrical contact member (242) may include various components, shapes, or materials as would be apparent to one having ordinary skill in the art in view of the teachings herein.

As mentioned above, insulative membrane (244) houses electrical contact member (242) and flexible pad (246). Insulative membrane (244) may be made from a sufficient material such that membrane (244) may fluidly isolate electrical contact member (242) from the exterior of membrane (244). Therefore, if an exterior portion of membrane (244) is exposed to a fluid, such as bodily fluid or a saline solution, that fluid will not penetrate membrane (244) toward electrical contact member (242). Insulative membrane (244) is also made from a material that may be punctured under sufficient pressure, such as when sharp contacts (252) are pushed against membrane (244) with sufficient force, as described herein. The properties of membrane (244) are also such that when punctured, membrane (244) may also form a seal around the puncture area, such that membrane (244) also resists fluid transfer through the punctured area. In the alternative, insulative membrane (244) may be made of a material the that has an occluded opening that may expand in response to contacts (252) being pressed through membrane (244) such that contact (252) may extend through the opening. Additionally, membrane (244) may be sufficiently elastic that after sharp contacts (252) are removed from membrane (244), such as when cartridge (234) is removed from channel (232), the punctured portion of membrane (244) self-closes around the puncture site to protect electrical contact member (242) from exposure to fluid. As can be seen in FIG. 10B, when sharp contacts (252) are coupled with contact member (242), membranes (244, 254) together form a barrier that may prevent fluid from interfering with the electrical connection between contacts (242, 252).

Figure 11A:
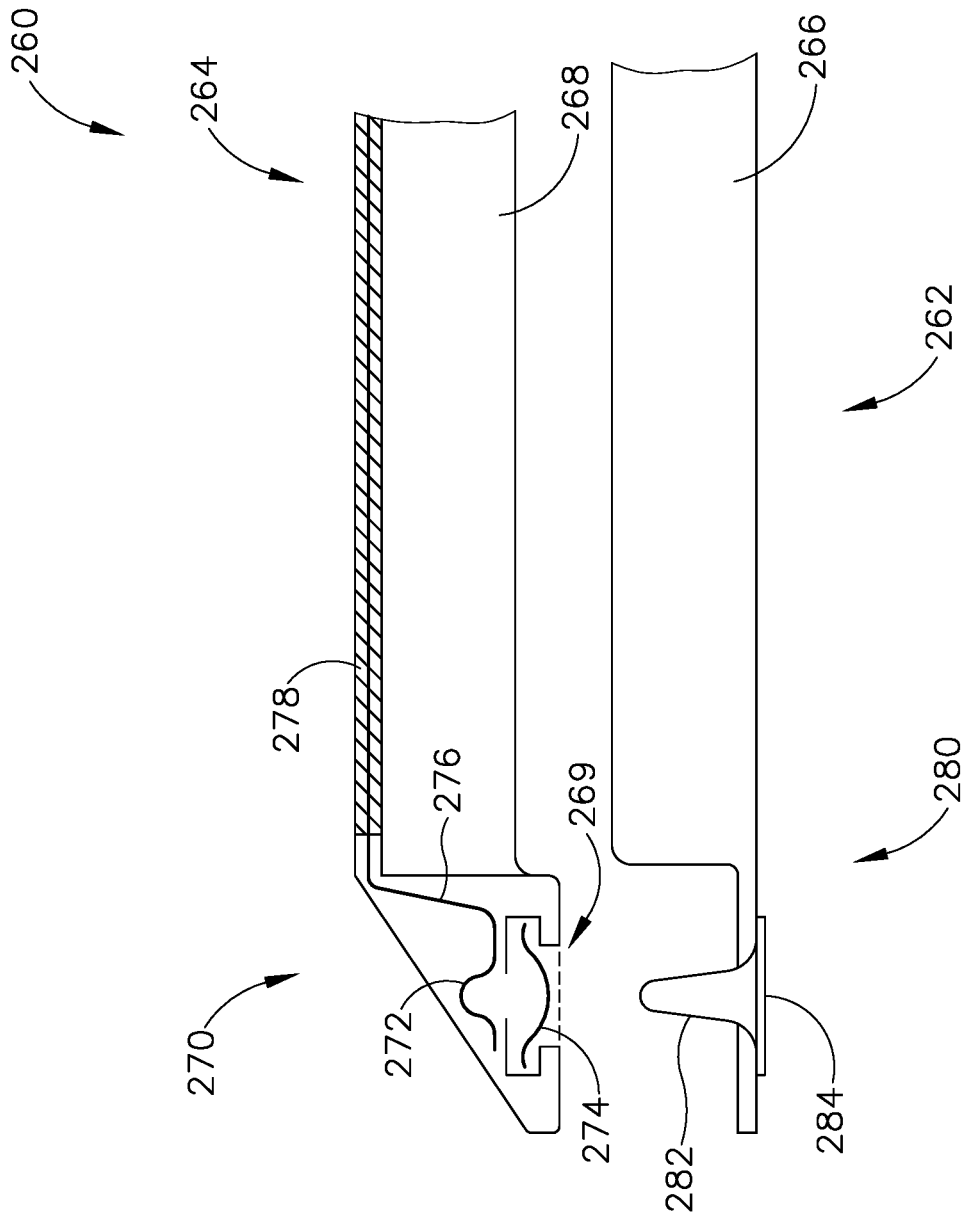
FIG. 11A depicts a cross-sectional view of an alternative cartridge and channel assembly that may be readily incorporated into the end effector of FIG. 8, where the cartridge is decoupled from the channel.
Figure 11B:
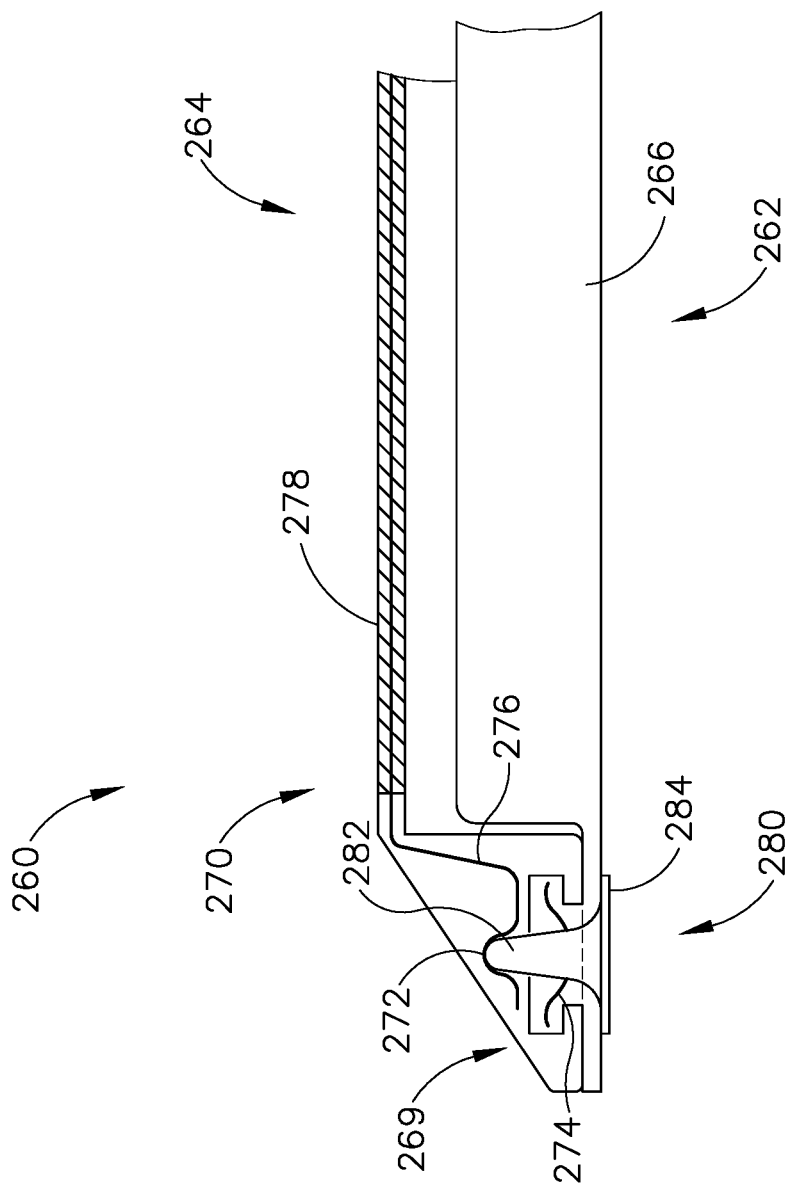
FIG. 11B depicts a cross-sectional view of the cartridge and channel assembly of FIG. 11A, where the cartridge is coupled with the channel.

FIGS. 11A-11B show another exemplary alternative cartridge and channel assembly (260) that may be readily incorporated into end effector (160) in replacement of cartridge (164) and channel (162), as described above, respectively. Cartridge and channel assembly (260) includes an elongate channel (262) and a staple cartridge (264). Channel (262) and cartridge (264) are substantially similar to channel (162) and cartridge (164), as described above, respectively, with difference elaborated below. In particular, FIG. 10A shows cartridge (264) decoupled from channel (262); while FIG. 10B shows cartridge (264) coupled with channel (232).

Channel (262) includes a channel body (266), and a channel contact assembly (280) located at the distal end of channel body (266). While in the current example, channel (262) only shows a single channel contact assembly (280), any suitable number of channel contact assemblies (280) may be utilized as would be apparent to one having ordinary skill in the art in view of the teachings herein.

Channel contact assembly (280) includes a contact member (282) and an electrical trace (284). Similar to electrical trace (182) described above, electrical trace (284) extends from contact member (282) through channel (262), and connects with shaft circuit board (134). Therefore, when shaft assembly (14) and handle assembly (12) are suitably coupled while power pack (44) powers handle assembly (12), electrical trace (284) may help provide electrically communication between electrical contact member (282) and power pack (44). While in the current example, electrical trace (284) is used to help establish electrical communication between contact member (282) of channel (262) and power pack (44), any other suitable structure may be used as would be apparent to one having ordinary skill in the art in view of the teachings herein. Contact member (282) is configured to electrically couple with contact member (272) when cartridge (264) is suitably coupled with channel (262). In particular, contact (282) is are configured to puncture a membrane (274) in order to electrically couple with contact member (272). When contact member (272) and contact (282) are electrically coupled, and when handle assembly (12) is suitably coupled with shaft assembly (14), power pack (44) may power electrically activated component (278).

Cartridge (264) includes a cartridge body (268) and a cartridge contact assembly (270). In the current example, cartridge body (268) defines a T-slot (269) dimensioned to house an insulative membrane (274). T-slot (269) is also dimensioned to receive a portion of contact member (282) such that contact (282) may puncture membrane (284) and electrically couple with contact member (272).

Cartridge contact assembly (270) includes an electrical contact member (272), an insulative membrane (244), an electrically activated component (278), and a connection (276) extending between contact member (272) and electrically activated component (278). The number of cartridge contact assemblies (270) may mirror the number of channel contact assemblies (280) such that there are corresponding contact assemblies (270, 280).

Electrical contact member (272) is configured to selectively receive a corresponding contact (282) in order to establish electrical communication between channel contact assembly (280) and cartridge contact assembly (270). Electrical contact member (282) may include various components, shapes, or materials as would be apparent to one having ordinary skill in the art in view of the teachings herein.

Insulative membrane (274) is located within T-slot (269) and may be formed of the same material as insulative membrane (224, 244) described above. Therefore, insulative membrane (274) and protects electrical contact (272) from fluids exterior to T-slot (269). Insulative membrane (274) is also made from a material that may be punctured under sufficient pressure, such as when contact (282) is pushed against membrane (274) with sufficient force, as described herein. The properties of membrane (274) are also such that when punctured, membrane (274) may also form a seal around the puncture area, such that membrane (274) also resists fluid transfer through the punctured area. Additionally, membrane (274) may be sufficiently elastic that after contact (282) are removed from membrane (274), such as when cartridge (264) is removed from channel (262), the punctured portion of membrane (274) self-closes around the puncture site to protect electrical contact member (272) from exposure to fluid. In the alternative, insulative membrane (274) may be made of a material the that has an occluded opening that may expand in response to contacts (282) being pressed through membrane (274) such that contact (282) may extend through the opening.

FIGS. 12-13 show another exemplary alternative cartridge channel assembly (300) that may be readily incorporated into end effector (160) in replacement of cartridge (164) and channel (162), as described above, respectively.

Cartridge and channel assembly (300) includes an elongate channel (302) and a staple cartridge (304). Channel (302) and cartridge (304) are substantially similar to channel (162) and cartridge (164) described above, with differences elaborated below. FIG. 12 shows cartridge (304) decoupled from channel (302); while FIG. 13 shows cartridge (304) coupled with channel (302).

Channel (302) includes a channel body (306) have two side walls each defining a recess (309), and a channel contact assembly (320) located within recesses (309). Channel contact assembly (320) includes a plurality of sharp contacts (322), and a plurality of corresponding electrical traces (324). Similar to electrical trace (182) described above, electrical traces (324) extend from a corresponding sharp contact (322), through channel (302), and connects with shaft circuit board (134). Therefore, when shaft assembly (14) and handle assembly (12) are suitably coupled while power pack (44) powers handle assembly (12), electrical traces (324) may help provide electrically communication between electrical contact member (322) and power pack (44). While in the current example, electrical traces (324) are used to help establish electrical communication between sharp contacts (322) of channel (302) and power pack (44), any other suitable structure may be used as would be apparent to one having ordinary skill in the art in view of the teachings herein. Sharp contacts (322) are configured to electrically couple with contact member (312) when cartridge (304) is suitably coupled with channel (302). In particular, sharp contacts (322) are configured to puncture a membrane (314) in order to electrically couple with contact member (312). When contact member (312) and sharp contacts (322) are electrically coupled, and when handle assembly (12) is suitably coupled with shaft assembly (14), power pack (44) may power electrically activated component (318).

Cartridge (304) includes a cartridge body (308) and a cartridge contact assembly (310). In the current example, cartridge body (308) includes a pair of laterally extending lugs or protrusions (307). Laterally extending lugs (307) are dimensioned to fit within a corresponding recess (309) defined by channel body (306). A portion of cartridge contact assembly (310) is located within laterally extending lug (307) in order to suitably couple with channel contact assembly (320).

Cartridge contact assembly (310) includes a female electrical contact member (312), an insulative membrane (314), an electrically activated component (318), and a connection (316) extending between contact member (312) and electrically activated component (318). The number of cartridge contact assemblies (310) may mirror the number of channel contact assemblies (320) such that there are corresponding contact assemblies (310, 320).

Electrical contact members (312) are housed within insulative membrane (314). Electrical contact member (312) is configured to selectively receive a corresponding sharp contact (322) in order to establish electrical communication between channel contact assembly (320) and cartridge contact assembly (310). Electrical contact member (312) may include various components, shapes, or materials as would be apparent to one having ordinary skill in the art in view of the teachings herein.

Insulative membranes (314) are attached to lugs (307) and face toward sharp contacts (322). Insulative membranes (314) protect contacts (312) from exposure to fluids. Insulative membrane (314) may be made from a sufficient material such that membrane (314) may fluidly isolate electrical contact member (312) from the exterior of membrane (314). Therefore, if an exterior portion of membrane (314) is exposed to a fluid, such as bodily fluid or a saline solution, that fluid will not penetrate membrane (314) toward electrical contact member (314). Insulative membrane (314) is also made from a material that may be punctured under sufficient pressure, such as when sharp contacts (322) are pushed against membrane (314) with sufficient force, as described herein. The properties of membrane (314) are also such that when punctured, membrane (314) may also form a seal around the puncture area, such that membrane (314) also resists fluid transfer through the punctured area. In the alternative, insulative membrane (314) may be made of a material the that has an occluded opening that may expand in response to contacts (322) being pressed through membrane (314) such that contact (222) may extend through the opening. Additionally, membrane (314) may be sufficiently elastic that after sharp contacts (322) are removed from membrane (314), such as when cartridge (304) is removed from channel (312), the punctured portion of membrane (314) self-closes around the puncture site to protect electrical contact member (312) from exposure to fluid. As can be seen in FIG. 13, when sharp contacts (322) are coupled with contact member (312), membrane (314) forms a barrier that may prevent fluid from interfering with the electrical connection between contacts (312, 322).

Figure 14:
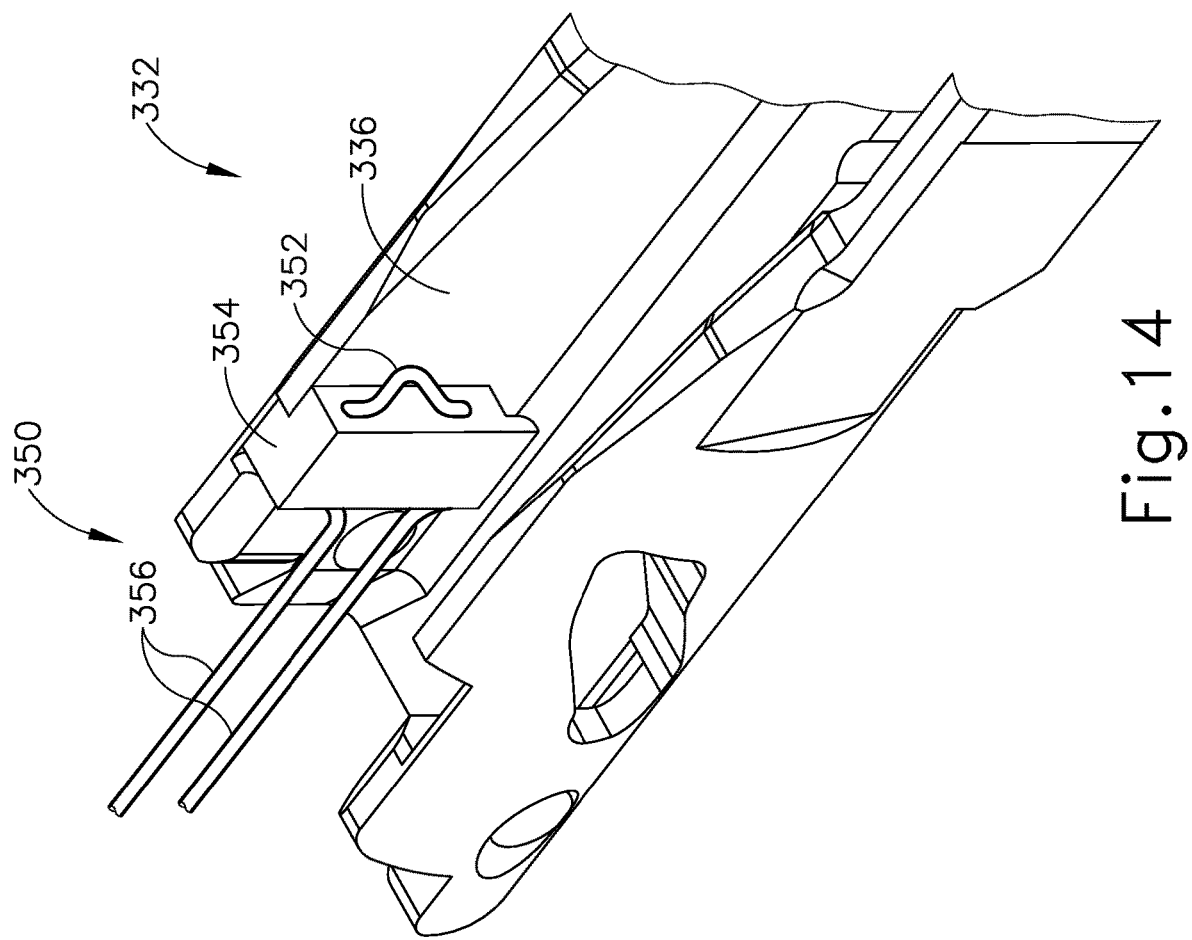
FIG. 14 depicts a perspective view of the proximal end of an alternative channel that may be readily incorporated into the end effector of FIG. 8.
Figure 15:
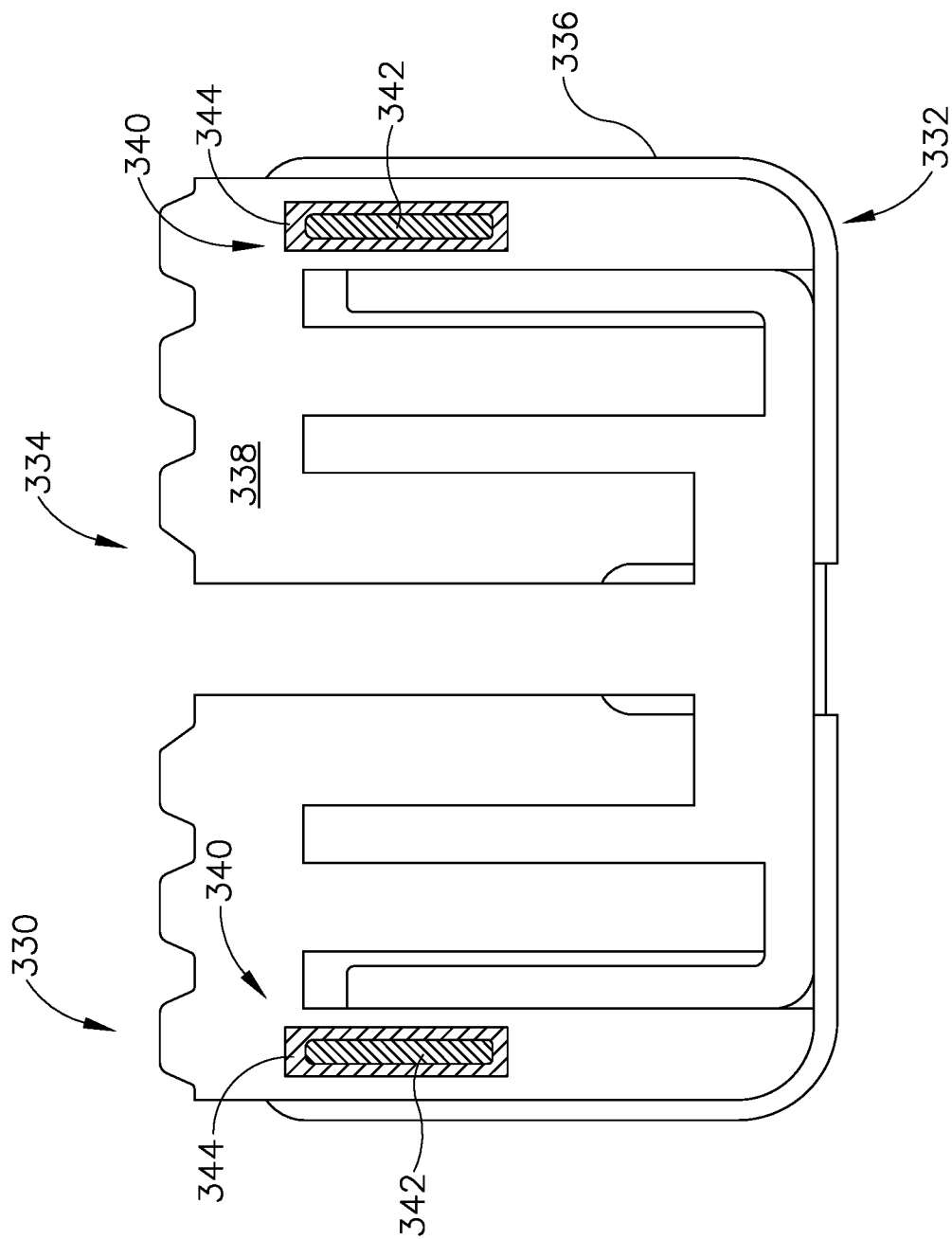
FIG. 15 depicts a cross-sectional end view of an exemplary cartridge coupled with the channel of FIG. 14.

FIG. 15 shows an alternative exemplary cartridge and channel assembly (330) that may be readily incorporated into end effector (160) in replacement of cartridge (164) and channel (162), as described above, respectively. Cartridge and channel assembly (330) include an elongate channel (332) and a staple cartridge (334). Channel (202) and cartridge (204) are substantially similar to channel (162) and cartridge (164) as described above, respectively, with differences elaborated below. As best shown in FIG. 14, channel (332) includes a channel body (336) and a channel contact assembly (350). Channel contact assembly (350) includes a contact member (352) extending distally from a retaining member (354), and electrical leads (356) extending proximally from retaining member (354). Contact member (352) is in electrical communication with electrical leads (356), while electrical leads (356) extend proximally and terminate into shaft circuit board (134). Similar to electrical traces (182), electrical leads (356) establish communication between shaft circuit board (134) and contact member (352). As best shown in FIG. 15, cartridge (334) includes a cartridge body (308) having a proximally presented face with insulative membranes (344) protecting female electrical contacts (342). While not shown, contacts (342) are in electrical communication with an electrically activated component. Contact member (352) is configured to penetrate membrane (344) in order to electrically couple with contact (342). Membranes (344) may be formed of the same or similar material as membranes (224) described above.

Figure 16:
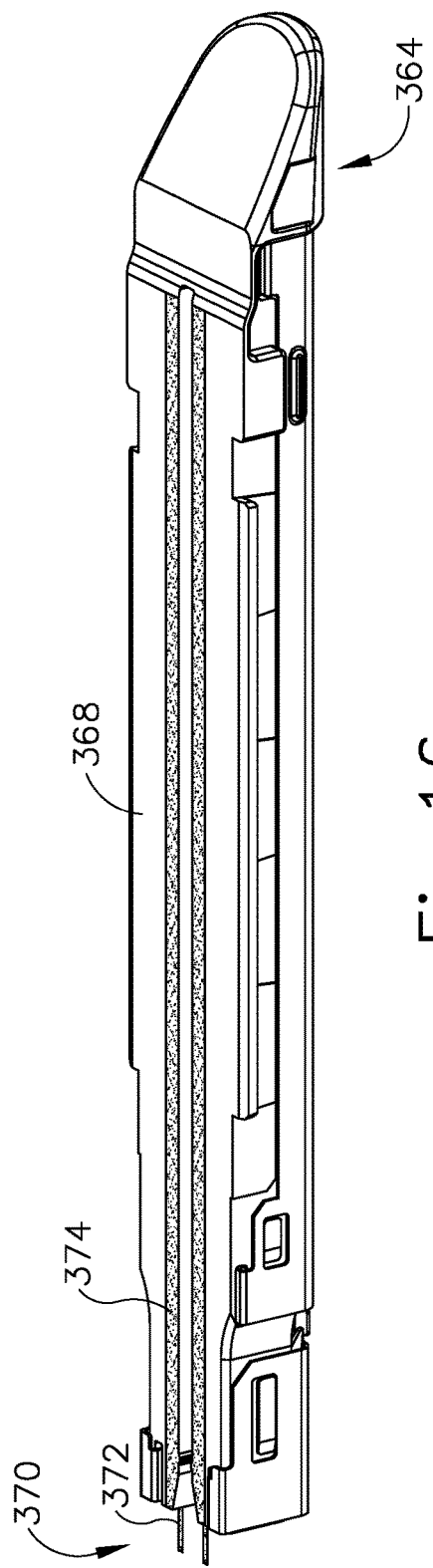
FIG. 16 depicts a perspective view of an alternative cartridge that may be readily incorporated into the end effector of FIG. 8.
Figure 17:
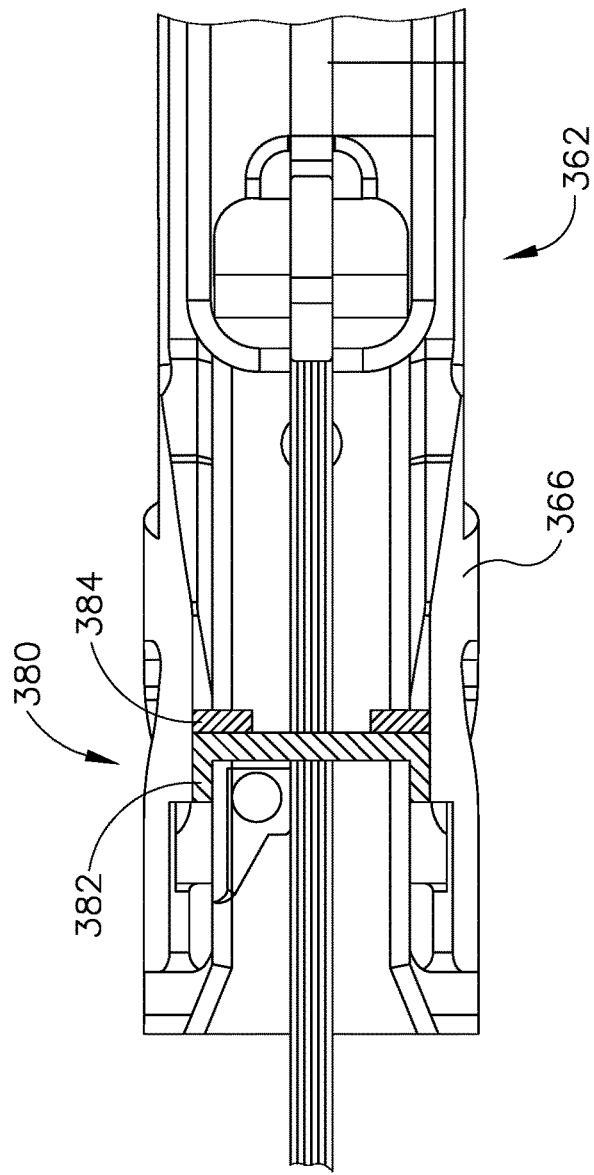
FIG. 17 depicts a top cross-sectional view of an alternative channel that may be readily incorporated into the end effector of FIG. 8 with the cartridge of FIG. 16.

FIGS. 16 and 17 show an alternative cartridge (364) and channel (362) that may be readily incorporated into end effector (160) in replacement of cartridge (164) and channel (162), as described above, respectively. Channel (362) and cartridge (364) are substantially similar to channel (302) and cartridge (304) as described above, respectively, with differences elaborated below. One particular difference is that cartridge (364) has sharp male electrical connectors (372) while channel (362) has a female electrical connector (382) protected by a membrane (384). As best shown in FIG. 16, cartridge (364) includes a cartridge body (368) having a proximally presented face with proximally facing male electrical contacts (372). Contacts (372) are in electrical communication with an electrically activated component (374). Sharp male connectors (372) are configured to penetrate membrane (384) in order to electrically couple with contact (382). Membranes (384) may be formed of the same or similar material as membranes (224) described above As best shown in FIG. 17, channel (362) includes a channel body (366) and a channel contact assembly (380). Channel contact assembly (380) includes female contact members (382) and electrical membranes (384) facing distally from female contact members (382). Membranes (384) act as a fluid barrier between female contacts (382) and the exterior environment. While not shown, channel (362) includes (354), and electrical leads (not shown) extending proximally from female electrical contacts (382). Electrical leads (not shown) provide electrical communication between female electrical contacts (382) and shaft circuit board (134).

B. Cartridges and Channels with Stationary Electrical Couplings

In some instances, it may be desirable to have at least one electrical contact between a cartridge and a channel move from an unexposed position to an exposed position based on whether a cartridge is suitably coupled with a channel. When the at least one electrical contact is in the unexposed position, the contact may be protected from unnecessary exposure to fluids. When the at least one electrical contact is in the exposed position, the contact may me in electrical communication with a corresponding electrical contact to complete an electrical circuit.

Figure 18:
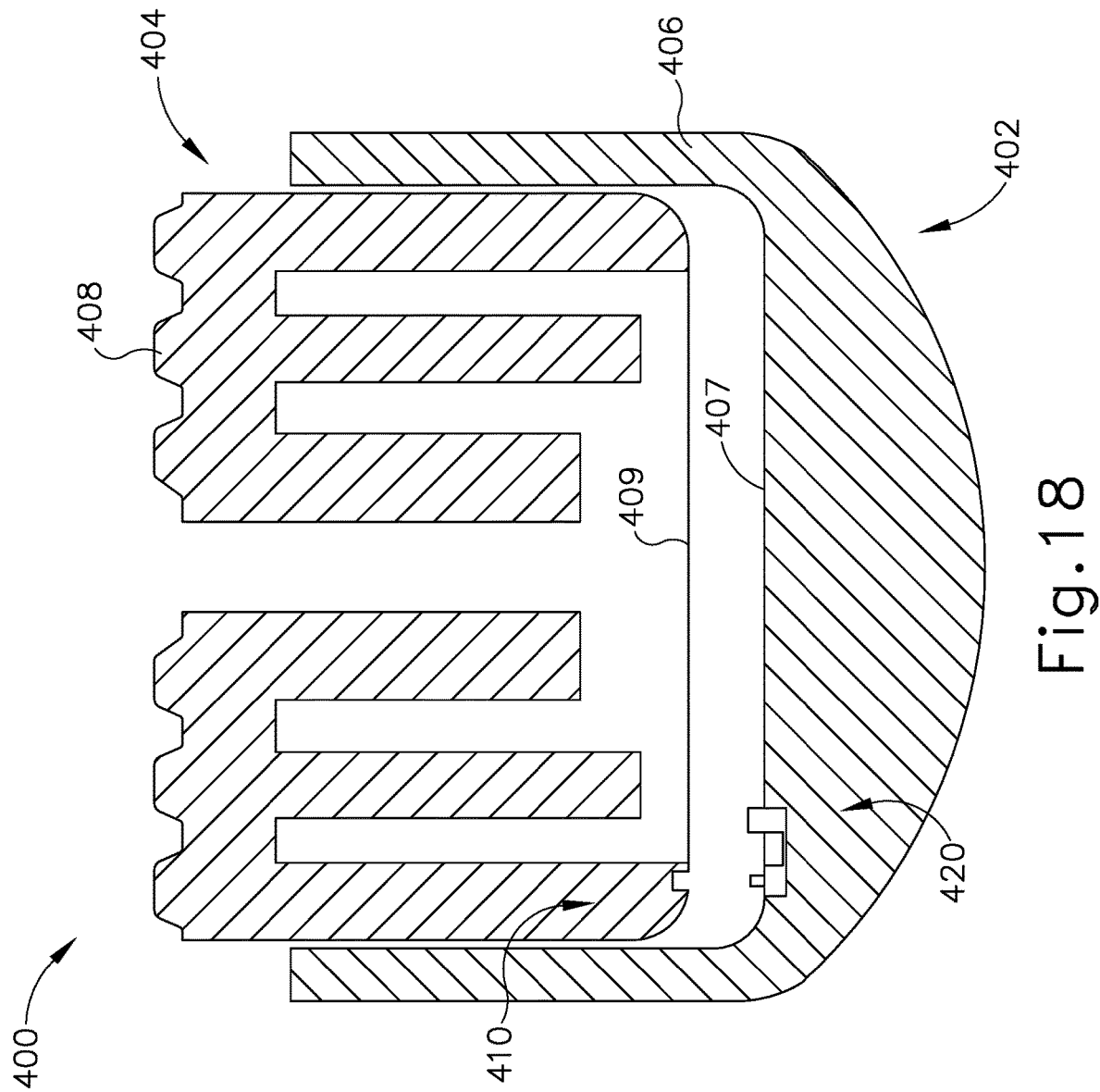
FIG. 18 depicts a cross-sectional end view of an alternative cartridge and channel assembly that may be readily incorporated into the end effector of FIG. 8, where the cartridge is decoupled from the channel.
Figure 19A:
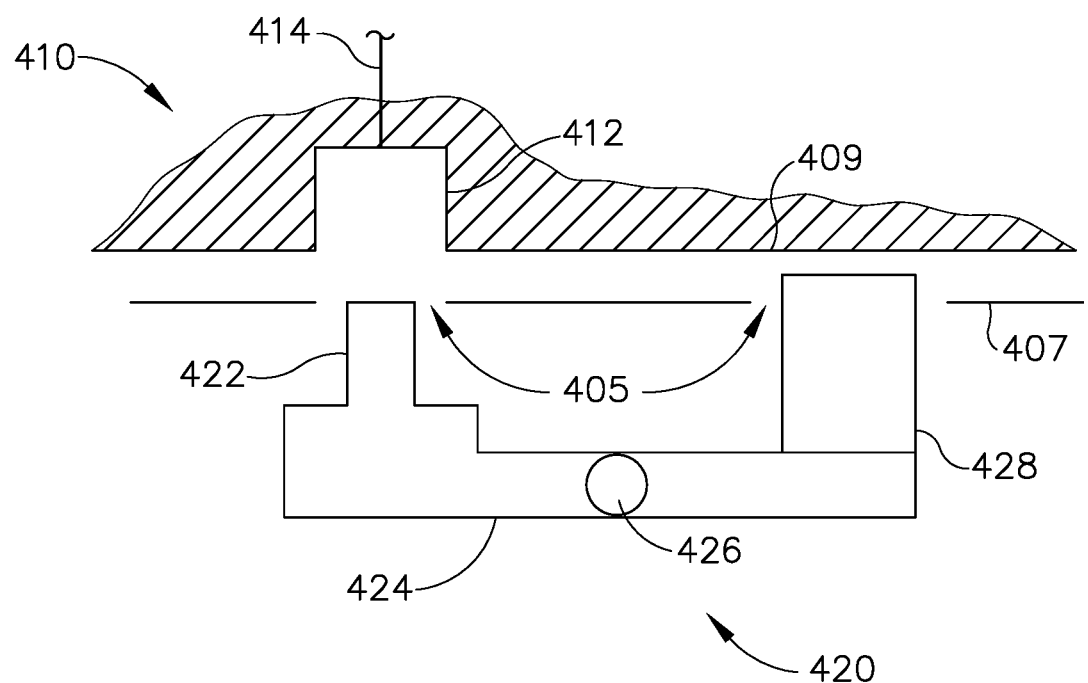
FIG. 19A depicts a cross-sectional view of an electrical contact assembly of the cartridge and channel assembly of FIG. 18, where the electrical contact assembly is decoupled.
Figure 19B:
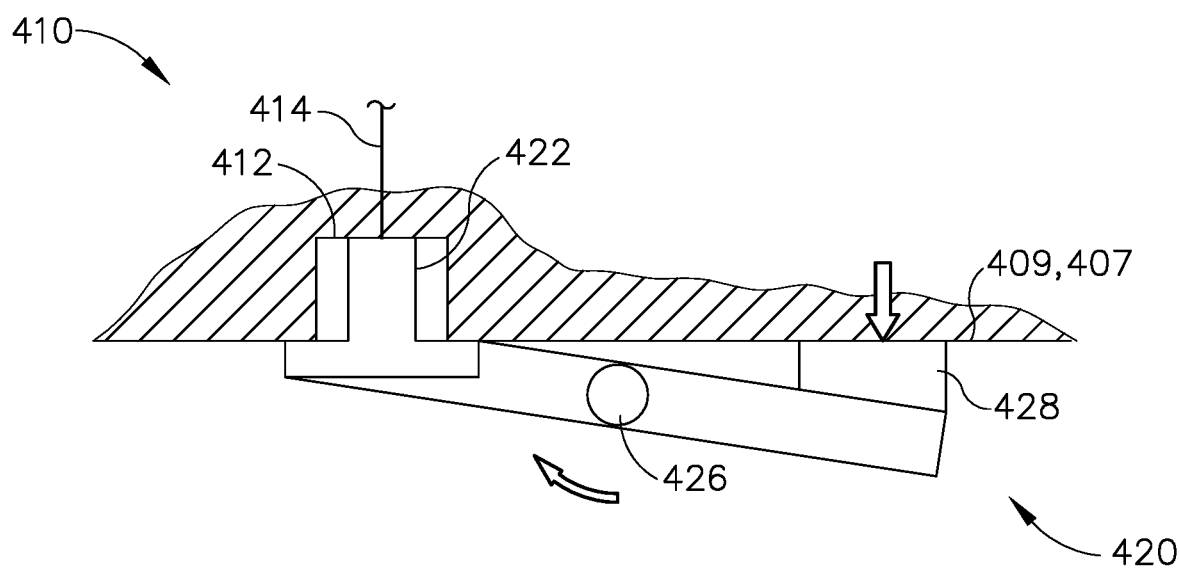
FIG. 19B depicts a cross-sectional view of the electrical contact assembly of FIG. 19A, where the electrical contact assembly is coupled.

FIGS. 18-19B show an exemplary alternative cartridge and channel assembly (400) that may be readily incorporated into end effector (160) described above. In particular, cartridge and channel assembly (400) includes an elongated channel (402) and a staple cartridge (404), which are substantially similar to channel (162) and staple cartridge (164) described above, respectively, with differences elaborated below.

Cartridge (404) includes a cartridge body (408) having a bottom surface (409), and a cartridge contact assembly (410). As will be described in greater detail below, bottom surface (409) of cartridge body (408) is configured to abut against selective portions of a channel contact assembly (420) in order to actuate portions of channel contact assembly (420) from an unexposed position to an exposed position, thereby allowing an electrical coupling between channel contact assembly (420) and cartridge contact assembly (410). Cartridge contact assembly (410) includes a female electrical contact (412) and a connection (414) extending from female electrical contact (412). While not shown in this example, connection (414) couples female electrical contact (412) with an electrically activated component (not shown), such as a sensor or a pad that transmits Radio Frequency (RF) energy to tissue. Female electrical contact (412) is located on a portion of cartridge body (408) in order to align with a portion of channel contact assembly (420) when cartridge (404) couples within channel (402).

Channel (402) includes a channel body (406) having an interior floor (407), and channel contact assembly (420). As best seen in FIG. 19A, channel body (406) defines a recess (405) that extends between two openings located on interior floor (407). Recess (405) of channel body (406) pivotably houses a portion of channel contact assembly (420).

Channel contact assembly (420) includes a male electrical contact (422), a pivot lever (424), a pivot point (426), and a non-electrical push switch (428). Pivot lever (424) is pivotably coupled within recess (405) of channel body (406) via pivot point (426). Pivot point (426) includes a torsional spring that biases pivot lever (424) to the position shown in FIG. 19A. While a torsional spring is used in the current example to bias pivot lever (424), any other biasing mechanism may be utilized as would be apparent to one having ordinary skill in the art in view of the teachings herein.

While not shown, male electrical contact (422) is coupled with an electrical trace (not shown), similar to electrical trace (182, 228, 256, 284, 324) or electrical leads (356) described above. Therefore, male electric contact (422) is in electrical communication with shaft circuit board (134) such that power pack (44) may power electrical contact (422) when shaft assembly (14) is suitably coupled with hand assembly (12).

Male electrical contact (422) is coupled to one portion of pivot lever (424) while non-electrical push switch (428) is coupled to the opposite portion of pivot lever (424). FIG. 19A shows male electrical contact (422) in an unexposed position while staple cartridge (404) is detached from elongate channel (402). A portion of non-electrical switch (428) extends upwardly from the corresponding opening defined by recess (405). While male electrical contact (422) is in the unexposed position, male electrical contact (422) is within the confines of recess (405) defined by channel body (406). While male electrical contact (422) is in the unexposed position, fluid may be prevented from being exposed to contact (422). The portion of recess (405) in which male electrical contact (422) is housed within may include a sealing membrane, formed of similar material as membrane (224) described above.

FIG. 19B shows male electrical contact (422) in the exposed position while staple cartridge (404) is attached to elongate channel (402). When cartridge (404) is suitably attached to elongate channel (402), bottom surface (409) abuts against non-electrical contact (428), thereby driving non-electrical contact (428) downward toward recess (405). Because non-electrical contact (428) is attached to pivot lever (424), pivot lever (424) pivots about pivot point (426), which in turn overcomes the biasing force provided by pivot point (426) to drive male electrical contact (422) upward away through opening defined by corresponding recess (405). Therefore, male electrical contact (422) is driven into the exposed position. Male electrical contact (422) electrically couples with female electrical contact (412) of cartridge (404) in order to establish an electrical connection between contacts (412, 422) in the exposed position. Therefore, when cartridge (404) is coupled with channel (402), male electrical contact (422) transitions from the unexposed position to the exposed position to electrically couple with female electrical contact (412).

Once cartridge (404) is used in accordance with the description above, cartridge (404) may be removed from channel (402), and torsional spring of pivot point (426) may rotate male electrical contact (422) back into the unexposed position. In other words, male electrical contact (422) may be configured to be in the exposed position when cartridge (404) is attached to channel (402), and electrical contact (422) may be configured to be in the unexposed position when cartridge (404) is not attached to channel (402). This may help prevent male electrical contact (422) from unnecessarily being exposed to fluids while cartridge (404) is not attached to channel (402)

In the current example, bottom surface (409) abuts against non-electrical contact (428) such that bottom surface (409) is flush with interior floor (407) of channel body (406). However, bottom surface (409) may also include a downwardly presented protrusion dimensioned to abut against non-electrical contact (428) such that the protrusion extends within opening defined by recess (405) to further drive non-electrical contact (428) within recess (405). Any other suitable surface on cartridge (404) may be used as would be apparent to one having ordinary skill in the art in view of the teachings herein. While one cartridge contact assembly (410) and one channel contact assembly (420) are shown in the current example, any suitable number of cartridge contact assemblies (410) and channel contact assemblies (420) may be used as would be apparent to one having ordinary skill in the art in view of the teachings herein.

Figure 20A:
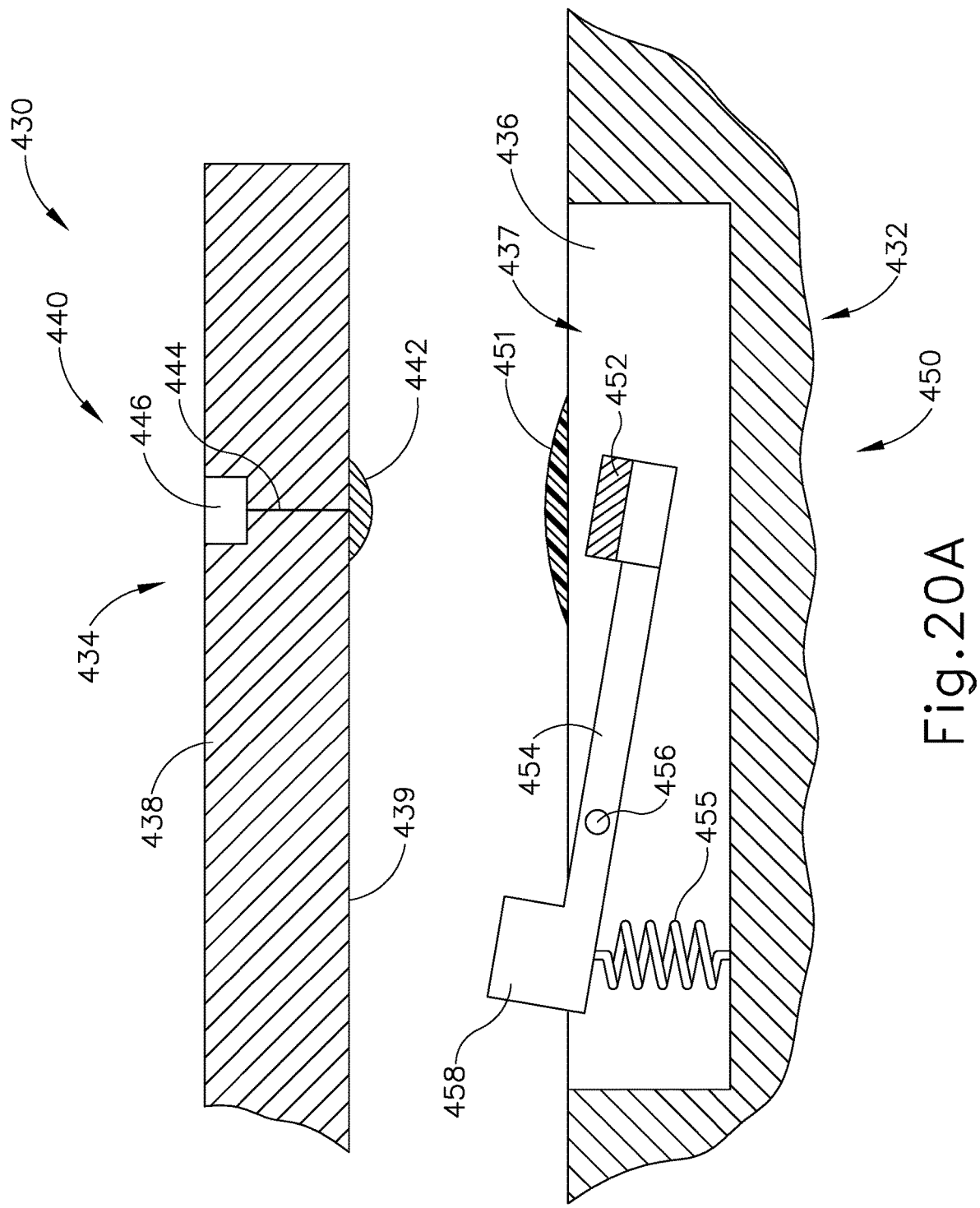
FIG. 20A depicts a cross-sectional view of an alternative cartridge and channel assembly that may be readily incorporated into the end effector of FIG. 8, where the cartridge is decoupled from the channel.
Figure 20B:
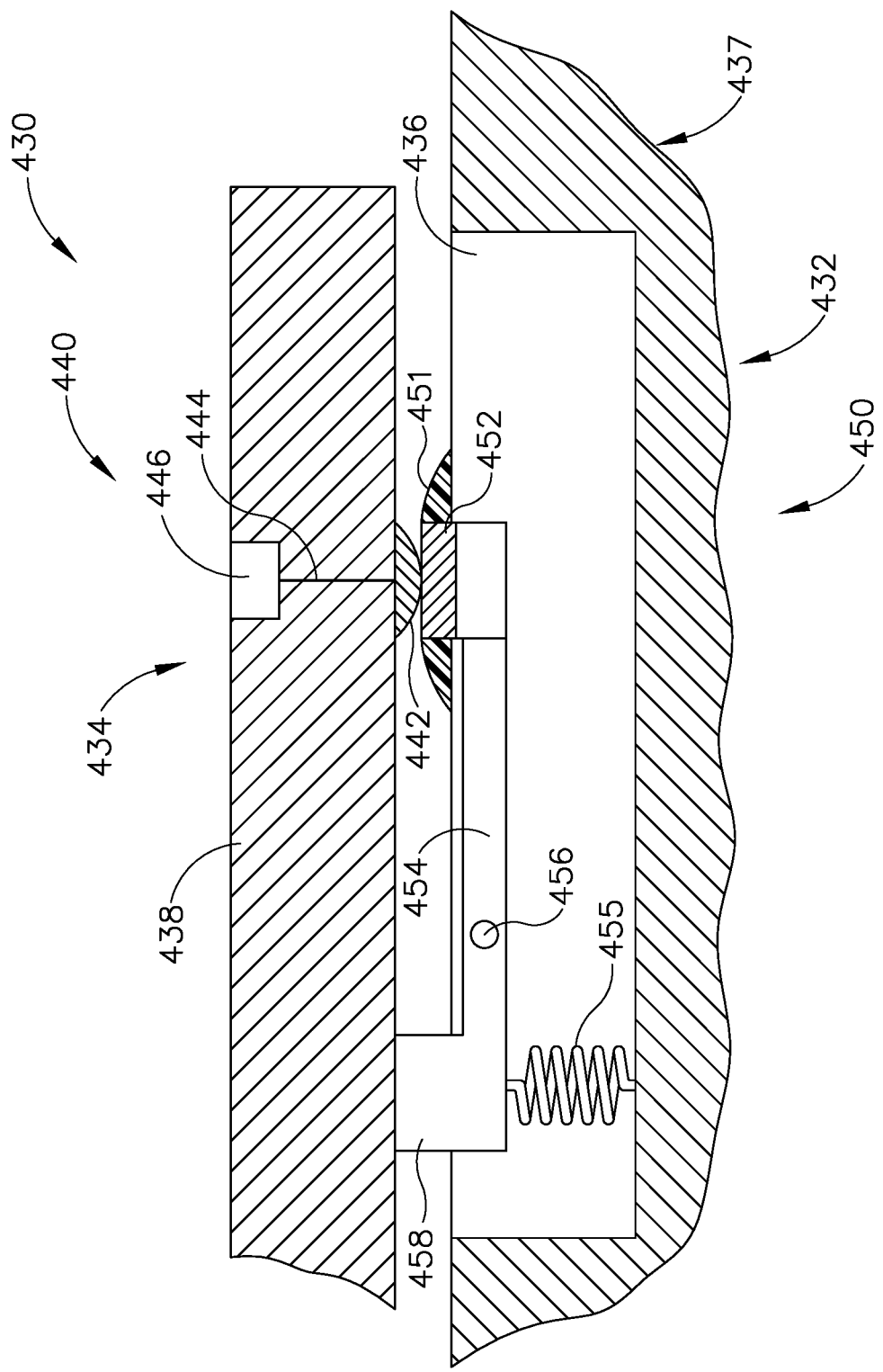
FIG. 20B depicts a cross-sectional view of the cartridge and channel assembly of FIG. 20A, where the cartridge is coupled with the channel.

FIGS. 20A-20B show another exemplary alternative cartridge channel assembly (430) that may be readily incorporated into end effector (160) described above. In particular, cartridge and channel assembly (430) includes an elongated channel (432) and a staple cartridge (434), which are substantially similar to channel (162) and staple cartridge (164) described above, respectively, with differences elaborated below.

Cartridge (434) includes a cartridge body (438) having a bottom surface (439), and a cartridge contact assembly (440). As will be described in greater detail below, bottom surface (439) of cartridge body (438) is configured to abut against selective portions of a channel contact assembly (450) in order to actuate portions of channel contact assembly (450) from an unexposed position to an exposed position, thereby allowing an electrical coupling between channel contact assembly (450) and cartridge contact assembly (440). Cartridge contact assembly (440) includes an electrical contact (442), an electrically activated component (446), and a connection (444) extending from electrical contact (442) toward electrically activated component (446). Electrically activated component (446) may include any electrical component that would be apparent to one having ordinary skill in the art in view of the teachings herein, such as a sensor or a pad that transmits Radio Frequency (RF) energy to tissue. Electrical contact (442) is located on a portion of cartridge body (438) in order to align with a portion of channel contact assembly (450) when cartridge (434) couples within channel (432). Channel (432) includes a channel body (436) defining a recess (437), and channel contact assembly (420). Recess (437) of channel body (436) pivotably houses a portion of channel contact assembly (450).

Channel contact assembly (450) includes an electrical contact (452), a pivot lever (454), a pivot point (456), a non-electrical push switch (458), a biasing spring (455), and a sealing membrane (451). Pivot lever (454) is pivotably coupled within recess (437) of channel body (436) via pivot point (456). Biasing spring (455) biases pivot lever (444) to the position shown in FIG. 20A. While biasing spring (455) is used in the current example to bias pivot lever (454), any other biasing mechanism may be utilized as would be apparent to one having ordinary skill in the art in view of the teachings herein.

While not shown, electrical contact (452) is coupled with an electrical trace (not shown), similar to electrical trace (182, 228, 256, 284, 324) or electrical leads (356) described above. Therefore, electric contact (452) is in electrical communication with shaft circuit board (134) such that power pack (44) may power electrical contact (452) when shaft assembly (14) is suitably coupled with hand assembly (12).

Electrical contact (452) is coupled to one portion of pivot lever (454) while non-electrical push switch (458) is coupled to the opposite portion of pivot lever (454). FIG. 20A shows electrical contact (452) in an unexposed position while staple cartridge (434) is detached from elongate channel (432). A portion of non-electrical switch (458) extends upwardly from recess (437). While electrical contact (452) is in the unexposed position, electrical contact (452) is within the confines of recess (437) defined by channel body (436). While electrical contact (452) is in the unexposed position, fluid may be prevented from being exposed to contact (452). Sealing membrane (451) may prevent fluids from entering into recess (437) and coming into contact with electrical contact (452). Sealing membrane (451) may be formed of similar material as membrane (224) described above.

FIG. 20B shows electrical contact (452) in the exposed position while staple cartridge (434) is attached to elongate channel (432). When cartridge (434) is suitably attached to elongate channel (432), bottom surface (439) abuts against non-electrical contact (458), thereby driving non-electrical contact (458) downward toward recess (437). Because non-electrical contact (458) is attached to pivot lever (454), pivot lever (454) pivots about pivot point (456), which in turn overcomes the biasing force provided by biasing spring (455) to drive electrical contact (452) upward away through opening defined by corresponding recess (437) and through membrane (451). Therefore, electrical contact (452) is driven into the exposed position. Electrical contact (452) electrically couples with electrical contact (442) of cartridge (434) in order to establish an electrical connection between contacts (442, 452) in the exposed position. Therefore, when cartridge (434) is coupled with channel (432), electrical contact (452) transitions from the unexposed position to the exposed position to electrically couple with electrical contact (442).

Once cartridge (434) is used in accordance with the description above, cartridge (434) may be removed from channel (432), and biasing spring (455) may rotate electrical contact (452) back into the unexposed position. In other words, electrical contact (452) may be configured to be in the exposed position when cartridge (434) is attached to channel (432), and electrical contact (452) may be configured to be in the unexposed position when cartridge (434) is not attached to channel (432). This may help prevent electrical contact (452) from unnecessarily being exposed to fluids while cartridge (434) is not attached to channel (432)

Bottom surface (439) may also include a downwardly presented protrusion dimensioned to abut against non-electrical contact (458) such that the protrusion extends within opening defined by recess (437) to further drive non-electrical contact (458) within recess (437). Any other suitable surface on cartridge (434) may be used as would be apparent to one having ordinary skill in the art in view of the teachings herein. While one cartridge contact assembly (440) and one channel contact assembly (450) are shown in the current example, any suitable number of cartridge contact assemblies (440) and channel contact assemblies (450) may be used as would be apparent to one having ordinary skill in the art in view of the teachings herein.

Figure 21:
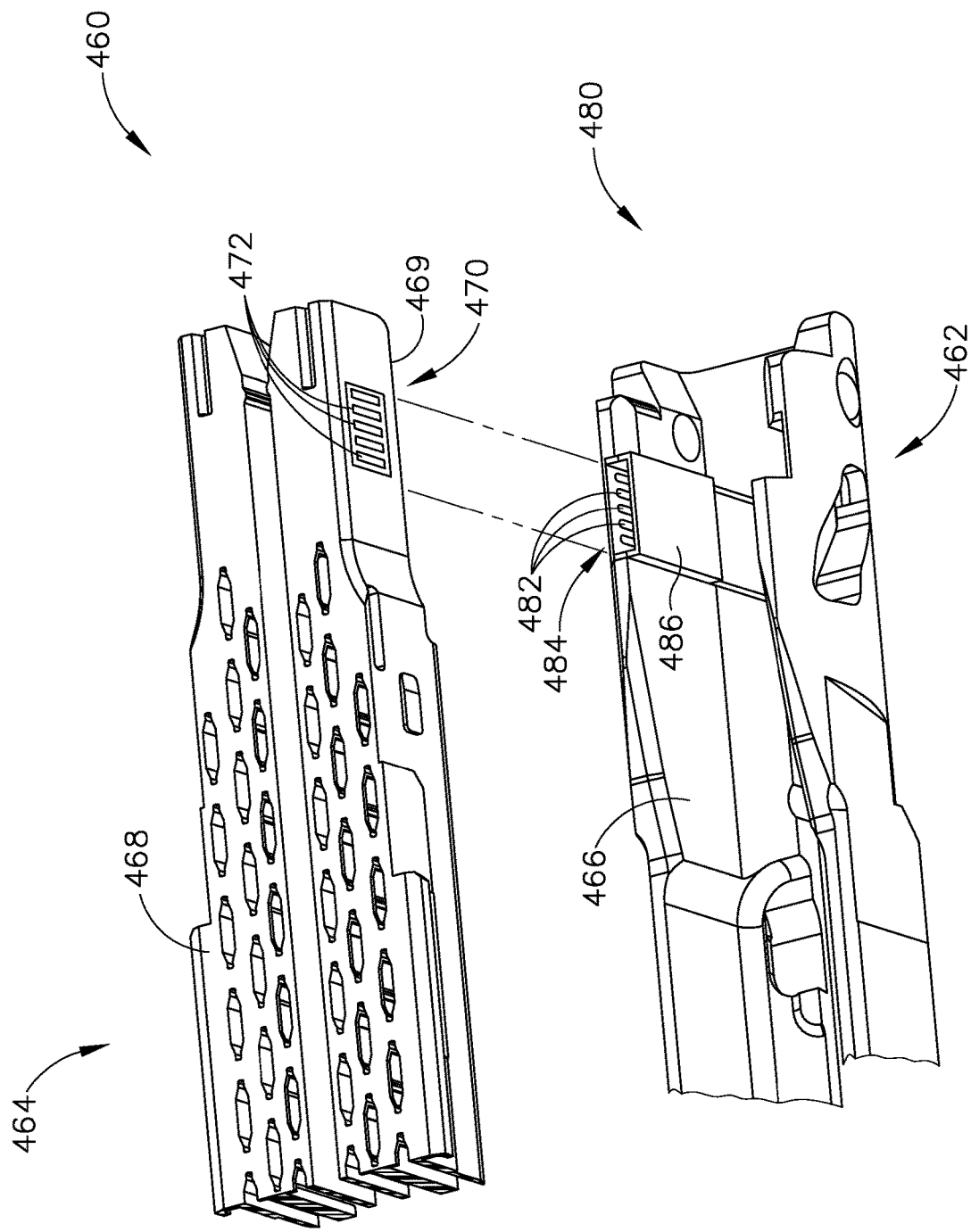
FIG. 21 depicts a partial perspective view of an alternative cartridge and channel assembly that may readily incorporated into the end effector of FIG. 8, where the cartridge is decoupled from the channel, where a sliding cover is in a first position.
Figure 22:
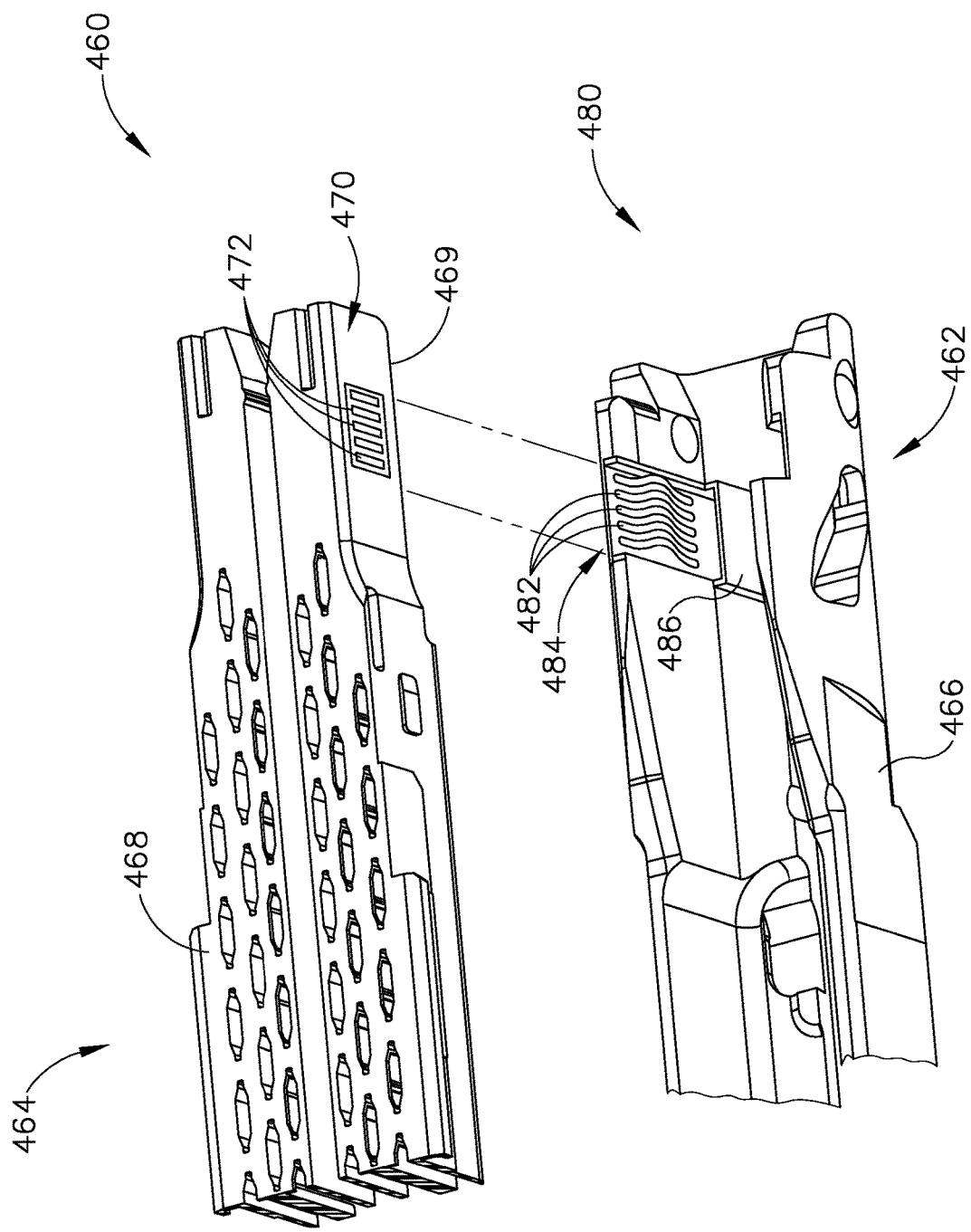
FIG. 22 depicts a partial perspective view of the cartridge and channel assembly of FIG. 21, where the cartridge is decoupled form the channel, where the sliding cover is in a second position.

FIGS. 21-22 show another exemplary alternative cartridge channel assembly (460) that may be readily incorporated into end effector (160) described above. In particular, cartridge and channel assembly (460) includes an elongated channel (462) and a staple cartridge (464), which are substantially similar to channel (162) and staple cartridge (164) described above, respectively, with differences elaborated below.

Staple cartridge (460) includes a cartridge body (468) having a camming surface (469), and a cartridge contact assembly (470). As will be described in greater detail below, camming surface (469) is configured to drive a sliding cover (486) from a protective position to an exposed position when staple cartridge (464) is attached to channel (462). Cartridge contact assembly (272) includes a plurality of electrical contacts (472). While not shown, electrical contacts (472) are also in electrical communication with at least one electrically activated component (not shown). The electrically activated component (not shown) may include any electrical component that would be apparent to one having ordinary skill in the art in view of the teachings herein, such as a sensor or a pad that transmits Radio Frequency (RF) energy to tissue.

Elongated channel (462) includes a channel body (466) and a channel contact assembly (480). Channel contact assembly (480) is located on an interior portion of a side wall of channel body (466). Channel contact assembly (480) includes a plurality of contacts (482) housed within a slot (484) defined by channel body (466), and a sliding cover (486). Sliding cover (486) is biased to the protective position (ash shown in FIG. 21). Sliding cover (486) is configured to protect the plurality of contacts (482) when cover (486) is in the protective position. Sliding cover (486) may include a sealing element interacting with slot (484) in order to prevent fluid exposure on contacts (482) when cover (486) is in the protective position.

As best seen in FIG. 22, when cartridge (464) is inserting within channel (462), camming surface (469) may abut against sliding cover (486) to drive sliding cover (486) downward to the exposed position. While sliding cover (486) is in the exposed position, contacts (472) may electrically couple with contacts (482). While not shown, contacts (482) are in electrically communication with electrical traces (not shown), which electrically couple contacts (482) with shaft circuit board (134). Therefore, when shaft (14) is suitably coupled with handle (12), power pack (44) may electrically activated contacts (482). When contacts (482) are electrically coupled with contacts (472) of cartridge (464), power pack (44) may power electrically activated component (not shown) of cartridge (464) via contacts (472, 482). Once cartridge (464) is used in accordance with the description herein, an operator may remove cartridge (464). The biased nature of sliding door (486) may actuate sliding door (486) within slot (484) back into the protected position, thereby preventing fluids from interfering with contacts (482). This may help prevent electrical contact (482) from unnecessarily being exposed to fluids while cartridge (464) is not attached to channel (462).

While in the current example, one channel contact assembly (480) and one cartridge contact assembly (470) are used, any suitable number of contacts assemblies (470, 480) may be utilized as would be apparent to one having ordinary skill in the art in view of the teachings herein.

Figure 23:
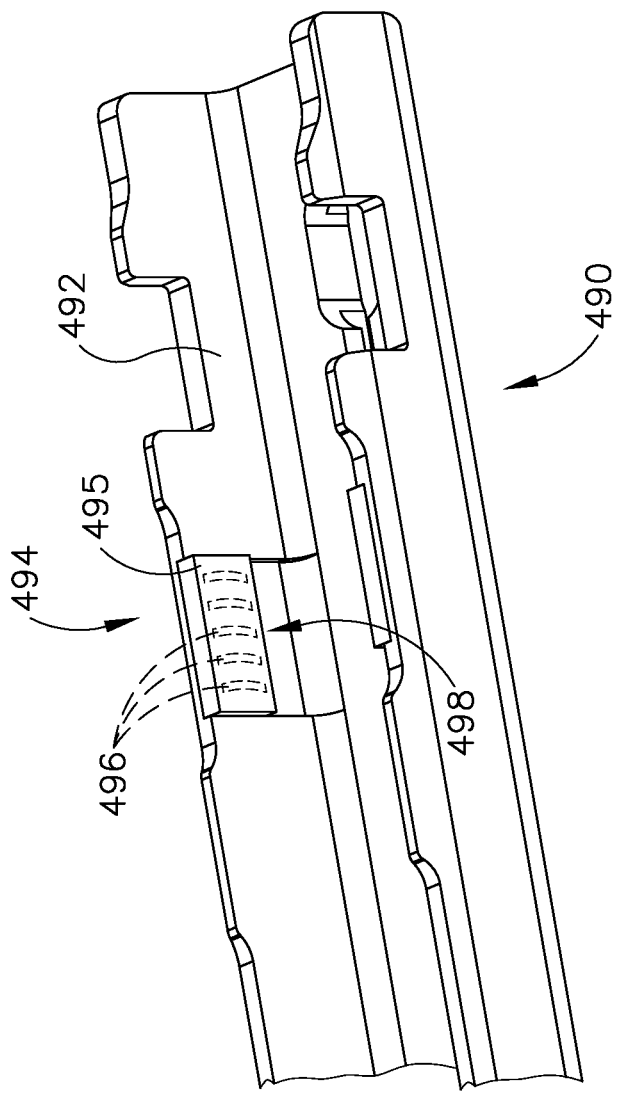
FIG. 23 depicts an alternative channel that may be readily incorporated into the end effector of FIG. 8.

FIG. 23 shows an alternative channel (490) that may be readily incorporated into cartridge and channel assembly (460) in replacement of channel (462) described above. Channel (490) includes a channel body (492) and a channel contact assembly (494), which are substantially similar to channel body (466) and channel contact assembly (480) described above, respectively, with differences elaborated below. Channel contacts assembly (494) includes a plurality of electrical contacts (496) which are substantially similar to contacts (482) described above. Channel contacts assembly (494) also includes a sliding cover (495) slidably disposed within slot (498) defined by channel body (492). Sliding cover (495) is configured to slide within slot (498) from a protective position to an exposed position. Sliding cover (495) may be substantially similar to sliding cover (486) described above, except that sliding cover (495) slide in a substantially vertical direction, as compared to the oblique direction that sliding cover (486) travels.

C. Alternative Sealing Connections Between Electrical Contacts

Figure 24:
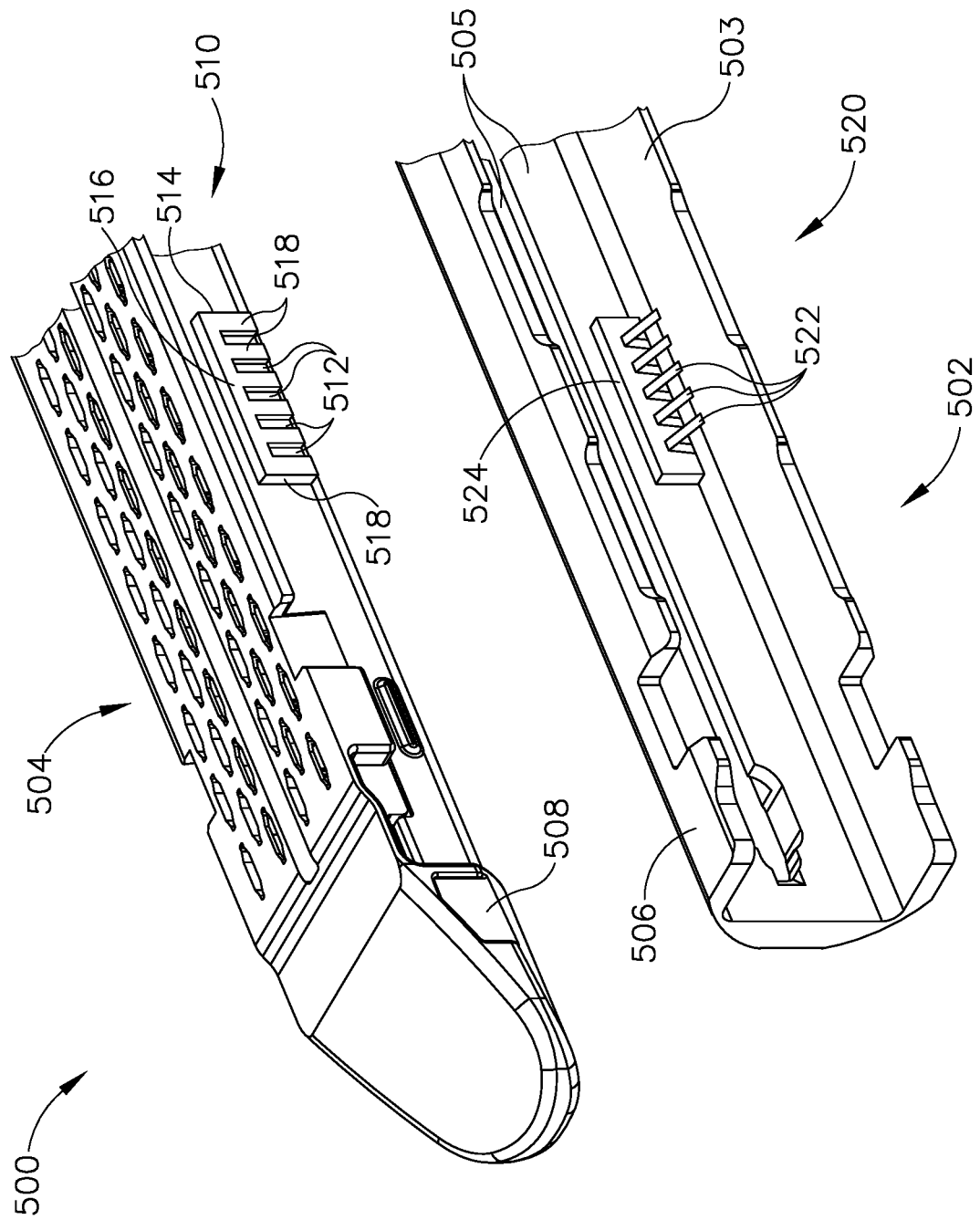
FIG. 24 depicts a perspective view of an alternative cartridge and channel assembly that may be readily incorporated into the end effector of FIG. 8, where the cartridge is decoupled from the channel.
Figure 25:
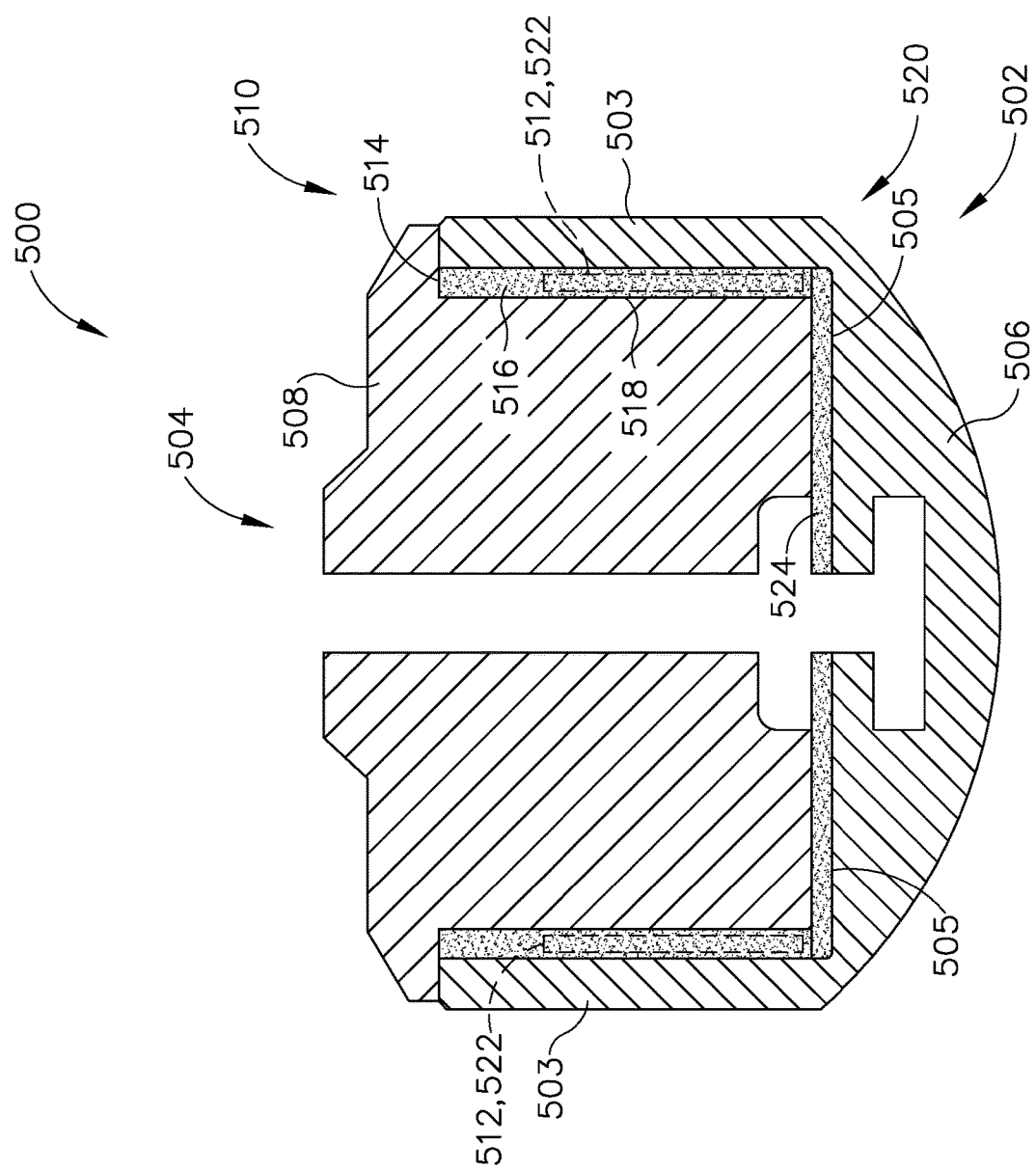
FIG. 25 depicts a cross-sectional end view of the cartridge and channel assembly of FIG. 24, where the cartridge is coupled with the channel.

FIGS. 24-25 show an exemplary alternative cartridge and channel assembly (500) that may be readily incorporated into end effector (160) described above. Cartridge and channel assembly (500) includes an elongated channel (502) and a staple cartridge (504), which are substantially similar to channel (162) and staple cartridge (164) described above, respectively, with differences elaborated below.

Channel (502) includes a channel body (506) and a contact assembly (520). Channel body (506) includes a pair of side walls (503) connected to each other by a base wall (505). Channel contact assembly (520) includes a plurality of contacts (522) and a floor sealing body (524). Floor sealing body (524) is fixed to base wall (505) of channel body (506). As will be described in greater detail below, floor sealing body (524) is configured to abut against selected portions of a sealing body (514) associated with cartridge (504) when cartridge (504) is suitably coupled with channel (502) such that contacts (512, 522) are protected from exposure to fluid.

While not shown, electrical contacts (522) are coupled with an electrical trace (not shown), similar to electrical trace (182, 228, 256, 284, 324) or electrical leads (356) described above. Therefore, electric contacts (522) are in electrical communication with shaft circuit board (134) such that power pack (44) may power electrical contact (522) when shaft assembly (14) is suitably coupled with hand assembly (12).

Cartridge (504) includes a cartridge body (508) and a cartridge contact assembly (510). Cartridge body (508) is configured to selectively couple with channel body (506). Cartridge contact assembly (510) includes a plurality of electrical contacts (512) and a sealing body (514). While not shown in this example, electrical contacts (512) are in electrical communication with an electrically activated component (not shown), such as a sensor or a pad that transmits Radio Frequency (RF) energy to tissue.

Sealing body (514) includes a longitudinally extending portion (516) extending above contacts (512), and a plurality of vertically extending portions (518) extending downward from longitudinally extending portion (516) between individual contacts (512). Vertically extending portions (518) are dimensioned to abut against floor sealing body (524) when cartridge (504) is suitably coupled with channel (502). Therefore, as best seen in FIG. 25, sealing body (514) and floor sealing body (524) fluidly isolate corresponding contacts (512, 522), as a pair, from the external environment, and from other contacts (512, 522), when cartridge (504) and suitably coupled with channel (502).

Figure 27:
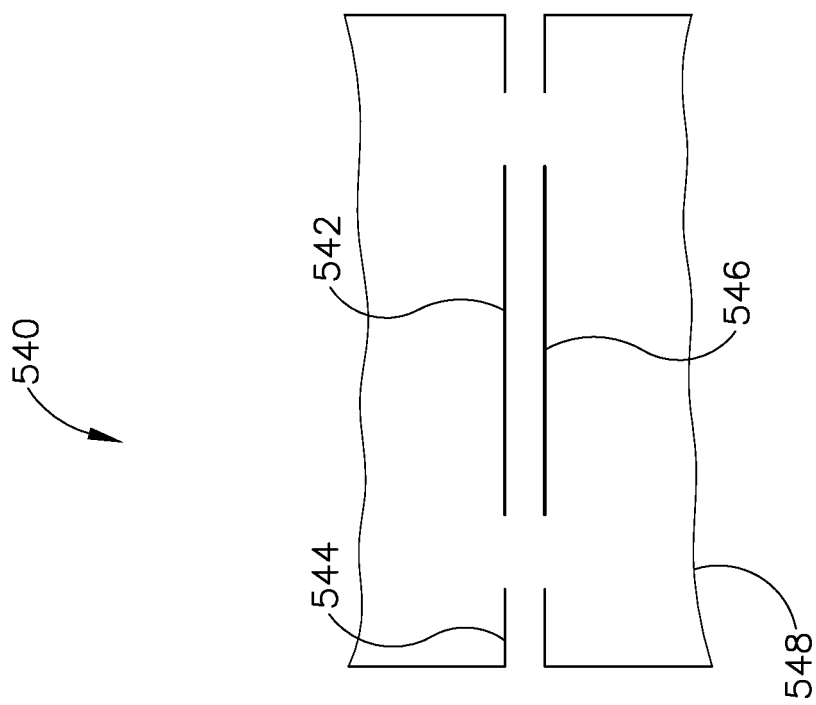
FIG. 27 depicts a cross-sectional end view of another alternative electrical contact assembly.
Figure 26:
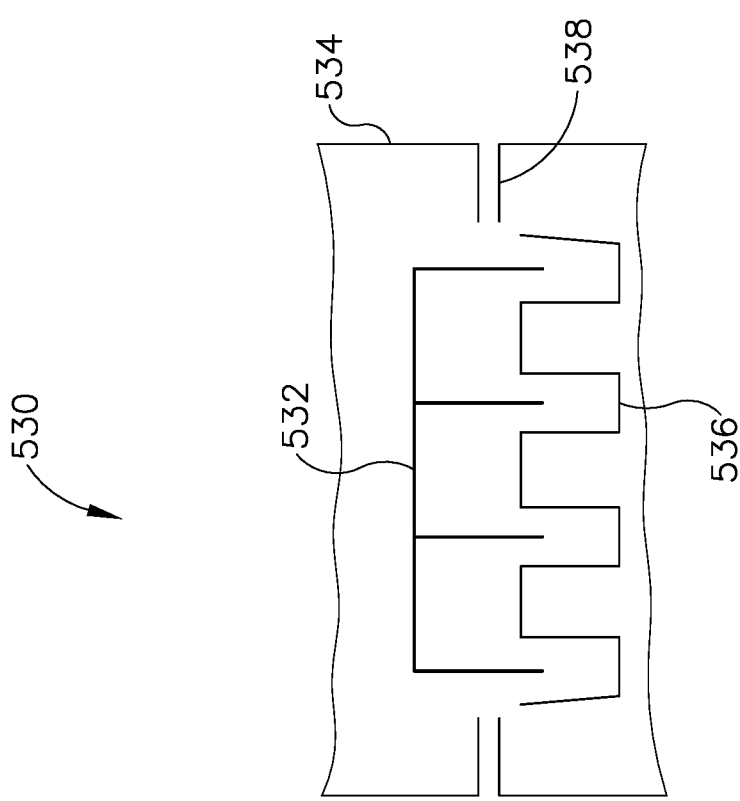
FIG. 26 depicts a cross-sectional end view of an alternative electrical contact assembly.

FIGS. 26 and 27 show other ways to seal contacts from an external environment. FIG. 26 shows an exemplary electrical contact assembly (530) that may be readily incorporated into end effector (160) described above in replacement of electrical contacts (174, 180) described above. Contact assembly (530) includes a plurality of male electrical contacts (532) surrounded by a sealing body (534), and a plurality of female electrical contacts (536) surrounded by its own sealing body (538). When contacts (532, 536) are coupled together, sealing bodies (534, 538) form a seal protecting contacts (532, 536) from exposure to fluid from the outside environment.

FIG. 27 shows an exemplary electrical contact assembly (540) that may be readily incorporated into end effector (160) described above in replacement of electrical contacts (174, 180) described above. Contact assembly (430) includes a first electrical contact (542) surrounded by a sealing body (544), and a second electrical contact (546) surrounded by its own sealing body (548). When contacts (542, 546) are coupled together, sealing bodies (544, 548) form a seal protecting contacts (542, 546) from exposure to fluid from the outside environment.

Figure 28B:
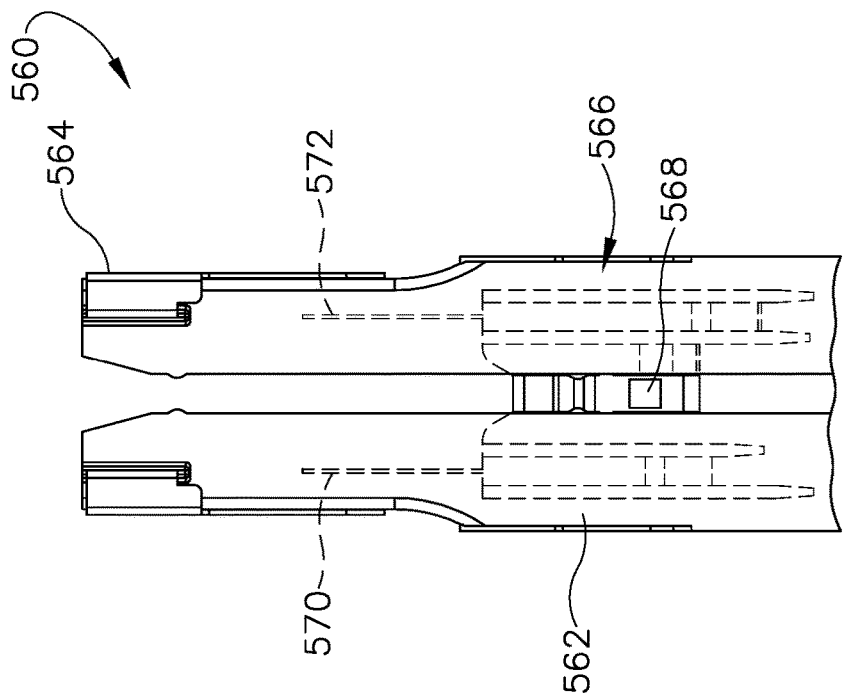
FIG. 28B depicts a top plan view of the cartridge of FIG. 28A, where the wedge sled is in a distal position.
Figure 28A:
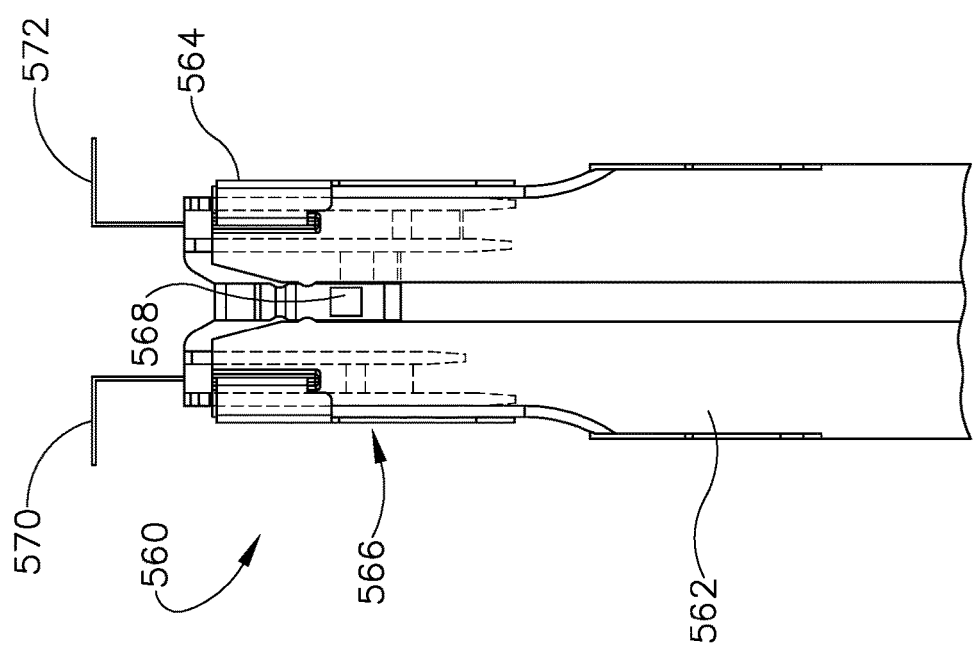
FIG. 28A depicts a top plan view of an alternative cartridge that may be readily incorporated into the end effector of FIG. 8, where a wedge sled is in a proximal position.

FIGS. 28A-28B show an exemplary staple cartridge (560) that may be readily incorporated into end effector (160) described above. Staple cartridge (560) includes a cartridge body (562) and a wedge sled (566) slidably disposed within cartridge body (562). Wedge sled (566) may be substantially similar to wedge sled (112) described above, with differences elaborated below. In particular, wedge sled (566) includes a chip (568) attached to a first connection (570) and a second connection (572). Chip (568) contains readable information on it, such as the cartridge type. First and second connection (570, 572) are plastically deformable. As shown in FIG. 28A, in a pre-fired position, first and second connection (570, 572) form a right angle to make a connection with electrical contacts of channel (162). At this moment, chip (568) may be read by shaft circuit board (134) since first and second connections (570, 572) are coupled with electrical contact of channel (162). With chip (568) in communication with electrical contacts of channel (162), shaft circuit board (134) may detect there is a valid, unused, cartridge assembly (560) coupled with channel (162). Once wedge sled (566) is fired, first and second connections (570, 572) may make contact with a proximal end (564) of cartridge body (562) such that connections (570, 572) no longer form a right angle. When wedge sled (566) is returned to the proximal position, connections (570, 572) will not be in electrical communication with electrical contacts of channel (162). Therefore, shaft circuit board (135) may assume either no cartridge (560) is loaded, or a used cartridge (560) is loaded, and a new cartridge (560) must be loaded.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a body comprising a power source; (b) a shaft assembly extending distally from the body; (c) an end effector, wherein the end effector comprises: (i) a channel assembly, and (ii) a cartridge assembly configured to selectively couple with the channel assembly, wherein the cartridge assembly comprises an electrically activated component; and (d) an electrical contact assembly configured electrically couple the power source with the electrically activated component of the cartridge assembly, wherein the electrical contact assembly comprises: (i) a first electrical contact associated with the channel assembly, (ii) a second electrical contact associated with the cartridge assembly, and (iii) an insulating membrane associated with either the first electrical contact or the second electrical contact, wherein the insulating membrane is configured to transition between a closed position and an opened position, wherein either the first electrical contact or the second electrical contact is configured to transition the insulating membrane to the opened position when the cartridge assembly is coupled to the channel assembly.

Example 2

The surgical instrument of Example 1, wherein either the first or the second electrical contact is configured to puncture the insulating membrane when transitioning the insulating membrane to the opened state.

Example 3

The surgical instrument of any one or more of Examples 1 through 2, wherein either the first or the second electrical contact is configured to puncture the insulating membrane when transitioning the insulating membrane to the opened state.

Example 4

The surgical instrument of any one or more of Examples 1 through 3, wherein the electrical contact assembly further comprises a flexible pad associated with the first electrical contact.

Example 5

The surgical instrument of any one or more of Examples 1 through 4, wherein the electrical contact assembly further comprises a flexible pad associated with the second electrical contact.

Example 6

The surgical instrument of any one or more of Examples 1 through 5, wherein the channel assembly defines a recess.

Example 7

The surgical instrument of any one or more of Examples 1 through 6, wherein the first electrical contact assembly is housed within the recess.

Example 8

The surgical instrument of any one or more of Examples 1 through 7, wherein the cartridge assembly further comprises a laterally extending lug, wherein the second electrical contact assembly is attached to the laterally extending lug.

Example 9

The surgical instrument of any one or more of Examples 1 through 8, wherein the cartridge assembly defines a T-slot, wherein the insulative membrane is housed within the T-slot.

Example 10

The surgical instrument of any one or more of Examples 1 through 9, wherein the shaft assembly is detachable from the body.

Example 11

The surgical instrument of Example 10, wherein the shaft assembly further comprises a proximal electrical connector, wherein the body comprises a distal electrical connector, wherein the proximal electrical connector is configured to electrically couple with the distal electrical connector when the shaft assembly is attached to the body.

Example 12

The surgical instrument of any one or more of Examples 1 through 11, wherein the electrically activated component comprises a sensor.

Example 13

The surgical instrument of any one or more of Examples 1 through 12, wherein the electrically activated component is configured to deliver Radio Frequency energy.

Example 14

The surgical instrument of any one or more of Examples 1 through 13, wherein the shaft assembly further comprises an electrical connecting member in electrical communication with the first electrical contact.

Example 15

The surgical instrument of Example 14, wherein the shaft assembly further comprises a shaft circuit board coupled with the electrical connecting member.

Example 16

A surgical instrument comprising: (a) a body comprising a power source; (b) a shaft assembly; (c) an end effector at a distal end of the shaft assembly, wherein the end effector comprises: (i) a channel assembly, and (ii) a cartridge assembly configured to selectively couple with the channel assembly, wherein the cartridge assembly comprises an electrically activated component; and (d) an electrical contact assembly configured electrically couple the power source with the electrically activated component of the cartridge assembly, wherein the electrical contact assembly comprises: (i) a first electrical contact associated with the channel assembly, wherein the first electrical contact is configured to actuate from a first position to a second position in response to the cartridge assembly selectively coupling with the channel assembly, (ii) a second electrical contact associated with the cartridge assembly, wherein the first electrical contact is configured to couple with the second electrical contact in the second position, and (iii) an insulating membrane associated with either the first electrical contact, wherein the first electrical contact is located within the insulating membrane in the first position.

Example 17

The surgical instrument of Example 16, wherein the first electrical contact is pivotably coupled with the channel assembly.

Example 18

The surgical instrument of any one or more of Examples 16 through 17, wherein the first electrical contact is biased to the first position.

Example 19

The surgical instrument of Example 18, further comprising a spring member configured to bias the first electrical contact into the first position.

Example 20

A surgical instrument comprising: (a) a body comprising a power source; (b) a shaft assembly extending distally from the body; (c) an end effector, wherein the end effector comprises: (i) a channel assembly defining a recess, and (ii) a cartridge assembly configured to selectively couple with the channel assembly, wherein the cartridge assembly comprises an electrically activated component, and (d) an electrical contact assembly configured electrically couple the power source with the electrically activated component of the cartridge assembly, wherein the electrical contact assembly comprises: (i) a first electrical contact associated with the channel assembly, wherein the first electrical contact is configured to actuate from a first position to a second position in response to the cartridge assembly selectively coupling with the channel assembly, wherein the first electrical contact is housed within the recess of the channel assembly in the first position, and (ii) a second electrical contact associated with the cartridge assembly, wherein the first electrical contact is configured to couple with the second electrical contact in the second position.

IV. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. application Ser. No. 15/934,139, entitled "Surgical Instrument with Compressible Electrical Connector," filed on Mar. 23, 2018, published as U.S. Pub. No. 2019/0290307 on Sept. 26, 2019; U.S. application Ser. No. 15/934,148, entitled "Seal for Surgical Instrument," filed on Mar. 23, 2018, published as U.S. Pub. No. 2019/0290308 on Sep. 26, 2019; U.S. application Ser. No. 15/934,173, entitled "Staple Cartridge with Short Circuit Prevention Features," filed on Mar. 23, 2018, published as U.S. Pub. No. 2019/0290271 on Sep. 26, 2019; U.S. application Ser. No. 15/934,180, entitled "Surgical Instrument with Capacitive Electrical Interface," filed on Mar. 23, 2018, published as U.S. Pub. No. 2019/0290272 on Sep. 26, 2019; and U.S. application Ser. No. 15/934,190, entitled "Slip Ring Assembly for Surgical Instrument," filed on Mar. 23, 2018, published as U.S. Pub. No. 2019/0290273 on Sep. 26, 2019. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. Pub. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a body comprising a power source;
   (b) a shaft assembly extending distally from the body;
   (c) an end effector, wherein the end effector comprises:
      (i) a channel assembly, and
      (ii) a cartridge assembly configured to selectively couple with the channel assembly, wherein the cartridge assembly comprises an electrically activated component; and
   (d) an electrical contact assembly configured electrically couple the power source with the electrically activated component of the cartridge assembly, wherein the electrical contact assembly comprises:
      (i) a first electrical contact associated with the channel assembly,
      (ii) a second electrical contact associated with the cartridge assembly, and
      (iii) an insulating membrane associated with either the first electrical contact or the second electrical contact, wherein the insulating membrane is configured to transition between a closed position and an opened position, wherein either the first electrical contact or the second electrical contact is configured to transition the insulating membrane to the opened position when the cartridge assembly is coupled to the channel assembly.

2. The surgical instrument of claim 1, wherein either the first or the second electrical contact is configured to puncture the insulating membrane when transitioning the insulating membrane to the opened state.

3. The surgical instrument of claim 1, wherein the insulating member defines an occluded opening configured to transition between the closed position and the opened position.

4. The surgical instrument of claim 1, wherein the electrical contact assembly further comprises a flexible pad associated with the first electrical contact.

5. The surgical instrument of claim 1, wherein the electrical contact assembly further comprises a flexible pad associated with the second electrical contact.

6. The surgical instrument of claim 1, wherein the channel assembly defines a recess.

7. The surgical instrument of claim 1, wherein the first electrical contact assembly is housed within the recess.

8. The surgical instrument of 1, wherein the cartridge assembly further comprises a laterally extending lug, wherein the second electrical contact assembly is attached to the laterally extending lug.

9. The surgical instrument 1, wherein the cartridge assembly defines a T-slot, wherein the insulative membrane is housed within the T-slot.

10. The surgical instrument of claim 1, wherein the shaft assembly is detachable from the body.

11. The surgical instrument of claim 10, wherein the shaft assembly further comprises a proximal electrical connector, wherein the body comprises a distal electrical connector, wherein the proximal electrical connector is configured to electrically couple with the distal electrical connector when the shaft assembly is attached to the body.

12. The surgical instrument of claim 1, wherein the electrically activated component comprises a sensor.

13. The surgical instrument of claim 1, wherein the electrically activated component is configured to deliver Radio Frequency energy.

14. The surgical instrument of claim 1, wherein the shaft assembly further comprises an electrical connecting member in electrical communication with the first electrical contact.

15. The surgical instrument of claim 14, wherein the shaft assembly further comprises a shaft circuit board coupled with the electrical connecting member.

16. A surgical instrument comprising:
   (a) a body comprising a power source;
   (b) a shaft assembly;
   (c) an end effector at a distal end of the shaft assembly, wherein the end effector comprises:
      (i) a channel assembly, and
      (ii) a cartridge assembly configured to selectively couple with the channel assembly, wherein the cartridge assembly comprises an electrically activated component; and
   (d) an electrical contact assembly configured electrically couple the power source with the electrically activated component of the cartridge assembly, wherein the electrical contact assembly comprises:
      (i) a first electrical contact associated with the channel assembly, wherein the first electrical contact is configured to actuate from a first position to a second position in response to the cartridge assembly selectively coupling with the channel assembly,
      (ii) a second electrical contact associated with the cartridge assembly, wherein the first electrical contact is configured to couple with the second electrical contact in the second position, and
      (iii) an insulating membrane associated with either the first electrical contact, wherein the first electrical contact is located within the insulating membrane in the first position.

17. The surgical instrument of claim 16, wherein the first electrical contact is pivotably coupled with the channel assembly.

18. The surgical instrument of claim 16, wherein the first electrical contact is biased to the first position.

19. The surgical instrument of claim 18, further comprising a spring member configured to bias the first electrical contact into the first position.

20. A surgical instrument comprising:
   (a) a body comprising a power source;
   (b) a shaft assembly extending distally from the body;
   (c) an end effector, wherein the end effector comprises:
      (i) a channel assembly defining a recess, and
      (ii) a cartridge assembly configured to selectively couple with the channel assembly, wherein the cartridge assembly comprises an electrically activated component, and
   (d) an electrical contact assembly configured electrically couple the power source with the electrically activated component of the cartridge assembly, wherein the electrical contact assembly comprises:
      (i) a first electrical contact associated with the channel assembly, wherein the first electrical contact is configured to actuate from a first position to a second position in response to the cartridge assembly selectively coupling with the channel assembly, wherein the first electrical contact is housed within the recess of the channel assembly in the first position, and
(ii) a second electrical contact associated with the cartridge assembly, wherein the first electrical contact is configured to couple with the second electrical contact in the second position.

* * * * *